(12) United States Patent
Figov et al.

(10) Patent No.: US 8,420,297 B2
(45) Date of Patent: *Apr. 16, 2013

(54) DEVELOPERS AND METHOD OF COLORING LITHOGRAPHIC PRINTING MEMBERS

(75) Inventors: Murray Figov, Ra'anana (IL); Ruizheng Wang, Rochester, NY (US); Moshe Marom, Herzlia (IL); Ilan Levi, Natanya (IL); Eynat Matzner, Adi (IL)

(73) Assignee: Eastman Kodak Company, Rochester, NY (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/860,149

(22) Filed: Aug. 20, 2010

(65) Prior Publication Data

US 2012/0045720 A1 Feb. 23, 2012

(51) Int. Cl.
*G03F 7/00* (2006.01)
*B41M 5/00* (2006.01)

(52) U.S. Cl.
USPC .................. 430/302; 101/463.1; 101/453

(58) Field of Classification Search .......... 430/270.1, 430/302; 101/450.1
See application file for complete search history.

(56) References Cited

U.S. PATENT DOCUMENTS

| | | | |
|---|---|---|---|
| 4,367,170 A * | 1/1983 | Uhlmann et al. | 252/586 |
| 6,022,909 A * | 2/2000 | Meinhardt et al. | 523/161 |
| 6,451,491 B1 | 9/2002 | Dhillon et al. | |
| 7,101,497 B2 * | 9/2006 | Tanaka et al. | 252/586 |
| 7,402,374 B2 | 7/2008 | Oohashi et al. | |
| 7,425,406 B2 | 9/2008 | Oshima et al. | |
| 7,462,440 B2 | 12/2008 | Yamasaki | |
| 2008/0003525 A1 * | 1/2008 | Amaya | 430/311 |
| 2008/0311521 A1 * | 12/2008 | Kazmaier et al. | 430/286.1 |
| 2010/0316956 A1 * | 12/2010 | Memetea et al. | 430/302 |

OTHER PUBLICATIONS

U.S. Appl. No. 12/483,323, filed Jun. 12, 2009, entitled Preparing Lithographc Printing Plates With Enhanced Contrast, by L. Memetea et al.

U.S. Appl. No. 12/481,002, filed Jun. 9, 2009, entitled Method of Providing Lithographic Printing Plates, by M. Figov et al.

* cited by examiner

*Primary Examiner* — Cynthia Kelly
*Assistant Examiner* — Chanceity Robinson
(74) *Attorney, Agent, or Firm* — J. Lanny Tucker

(57) ABSTRACT

A color contrast image in imaged lithographic printing precursors can be obtained by contacting the imaged precursor with a coloration solution containing a colorless form of a photochromic compound. Residual amounts of this compound attached to the oleophilic surface of the imaged precursor can be changed to its colored form when exposed to UV light. The coloration solution can be an alkaline or acidic developer or an alkaline or acidic solution used separately after development. The coloration solution can also be a gum solution.

18 Claims, No Drawings

DEVELOPERS AND METHOD OF COLORING LITHOGRAPHIC PRINTING MEMBERS

FIELD OF THE INVENTION

This invention relates to a method for providing a visible color on the image formed in lithographic printing members that are derived from lithographic printing precursors. The invention also provides both acidic and alkaline coloration solutions (developers) designed for this purpose.

BACKGROUND OF THE INVENTION

In conventional or "wet" lithographic printing, ink receptive regions, known as image areas, are generated on a hydrophilic surface. When the surface is moistened with water and lithographic printing ink is applied, the hydrophilic regions retain the water and repel the ink, and the ink receptive regions accept the ink and repel the water. The ink is eventually transferred to the surface of a material upon which the image is to be reproduced.

Lithographic printing precursors useful for preparing lithographic printing plates or sleeves typically comprise one or more imageable layers applied over the hydrophilic surface of a substrate. The imageable layers include one or more radiation-sensitive components that can be dispersed in a suitable binder. Alternatively, the radiation-sensitive component can also be the binder material. Following imaging, either the imaged regions or the non-imaged regions of the imageable layer are removed by a suitable developer, revealing the underlying hydrophilic surface of the substrate. If the imaged regions are removed, the precursor is considered as positive-working. Conversely, if the non-imaged regions are removed, the precursor is considered as negative-working. In each instance, the regions of the imageable layer (that is, the image areas) that remain are ink-receptive, and the regions of the hydrophilic surface revealed by the developing process accept water and aqueous solutions, typically a fountain solution, and repel ink.

Direct digital imaging has become increasingly important in the printing industry. Lithographic printing precursors for the preparation of lithographic printing plates have been developed for use with infrared lasers that image in a platesetter in response to signals from a digital copy of the image in a computer. This "computer-to-plate" technology has generally replaced the former technology where masking films were used to image the precursors.

Lithographic printing plates can contain a colorant (dye or pigment) in the radiation-sensitive composition that has the function of making the image visible so it can be evaluated by optical density measurements before being mounted on press. Such colorants provide contrast between the image and the background. Some lithographic printing precursors cannot contain a colorant. For example, imaged lithographic printing plate precursors that are usually developed on-press have a colorless coating because if a colorant is present, it could contaminate the lithographic printing ink and the fountain solution used for development and printing, with the result of altering the printed color shades. However, sometimes it is necessary for such lithographic printing plates to be used the same way as those developed off-press, and in such instances, the image must be seen to be evaluated.

Other lithographic printing precursors contain materials that are not compatible with contrast-providing colorants. Such lithographic printing precursors have a faint colored image that is difficult to distinguish from the anodized aluminum substrate background. This low image contrast makes it almost impossible to evaluate the resulting lithographic printing plates for image quality, such as image resolution as measured using optical density measurements before mounting the plates onto a press. Such "colorless" lithographic printing plates are also difficult to "register" (align) when mounting them onto a press. Image registration (alignment) is very important in color printing in order to ensure image sharpness (resolution) and correct tinting shades.

It is a well known phenomenon that offset lithographic printing members containing sufficient coloration to be visible and measureable, when subjected to a development step, can leave significant contaminants of the coloration dye within the developer unit and such coloration has been tolerated as an inevitable part of the process. While any resinous material left within the developer unit has to be removed, dye residues turn the entire developer colored and cannot be so easily removed. Thus, there is a need to provide color contrast in lithographic printing members without causing such problems.

U.S. Pat. No. 6,451,491 (Dhillon et al.) describes the high loading of contrast-providing pigments into the imaging layer of lithographic printing plates. Such high amounts of pigments can destabilize imaging chemistry or developers.

Other contrast-providing colorants for lithographic printing members are obtained from leuco dyes that become colored in the presence of an acid or thermal acid generator, as described for example, in U.S. Pat. No. 7,402,374 (Oohashi et al.), U.S. Pat. No. 7,425,406 (Oshima et al.), and U.S. Pat. No. 7,462,440 (Yamasaki). These lithographic printing members have some disadvantages. For example, the acid or radical forming mechanism can be triggered prematurely during the drying of the printing plate, leading to un-wanted color, especially in on-press developed printing plates. Alternatively, many times the colored form of the dye is a salt that is soluble in water, leading to excessive coating loss if the imaged printing precursor is developed in aqueous developer. In some instances when the coating and the color is washed off in developer, some of the colored forms of the dyes, especially the triarylmethane dyes are light sensitive and require additional precautions in handling the lithographic printing plates. Lastly, a high concentration of the leuco dye and the latent acid must be added to the coating to ensure a good contrast between the image and background (OD 0.8-1.00). These components adversely affect the shelf-life, mechanical properties, and run-length of the photosensitive coating.

In copending and commonly assigned U.S. Ser. No. 12/483,323 (filed Jun. 12, 2009 by Memetea, Huang, Munnelly, and Wertz), a method is described for treating a lithographic printing precursor having an optical density of $OD_1$. After imaging, a coloring fluid is applied such that the optical density in the exposed regions is $OD_2$ that is greater than $OD_1$. The coloring fluid comprises a water-insoluble colorant and a solvent that is capable of swelling the exposed imageable layer.

An alternative approach is to add a dye such as Crystal Violet to the processing liquid (developer). While this does always provide the required effect, it causes considerable contamination of the processor.

Copending and commonly assigned U.S. Ser. No. 12/481,002 (filed Jun. 9, 2009 by Figov, Marom, and Levi) describes the use of spirolactams or spirolactones in the processing liquid (developer). These compounds are meant to be colorless in the liquid and to become colored when the pH is decreased.

There is a need for an improved means for providing contrast between the image and background of lithographic print-

SUMMARY OF THE INVENTION

The present invention provides a method for providing a lithographic printing plate comprising:

A) imagewise exposing a lithographic printing precursor comprising a substrate and an imageable layer to provide an imaged precursor having exposed and non-exposed regions in the imageable layer, B) contacting the imaged precursor with a coloration solution containing a photochromic compound, and C) exposing the imaged precursor after step B to ultraviolet (UV) light to effect color change of the photochromic compound attached to the imageable layer.

This invention also provides an alkaline coloration solution (developer) that has a pH of from about 10 to about 14, and comprising a photochromic compound that is represented by the following Structure (I):

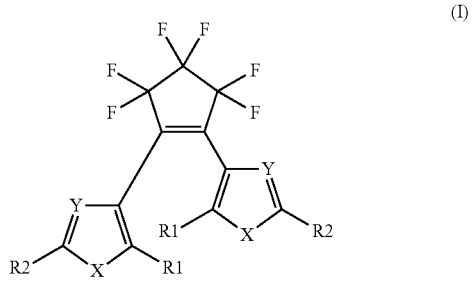

wherein X is oxygen, sulfur, sulfone, or a substituted or unsubstituted nitrogen, Y is oxygen or a substituted or unsubstituted carbon, $R^1$ is an electron donating group, and $R^2$ is hydrogen or any other substituent. Details of Structure (I) are provided below.

Further, this invention provides an acidic coloration solution that has a pH of from about 4.5 to about 7.5 and comprising a photochromic compound that is represented by Structure (I) shown above.

This invention provides a method of treating lithographic printing members with a coloration solution that contains a colorless form of a UV-sensitive photochromic material that attaches itself to the imaged areas on the printing surface. The colorless compound is then exposed to ultraviolet radiation, for example using a UV exposure unit in the processor, to cause a change in the colorless compound to provide a colored compound, thereby providing a color image that can be evaluated in a suitable manner. For example, the invention can be used to provide color contrast in imaged lithographic printing members. Negative-working lithographic printing precursors are particularly useful.

While the coloration solution can be used after conventional alkaline development, the coloration solution can also be an acidic or alkaline processing solution (developer) used after imaging.

The UV-sensitive photochromic compounds used in this invention have specific properties that are suitable for the intended purpose, which properties are described in more detail below.

DETAILED DESCRIPTION OF THE INVENTION

Definitions

Unless the context indicates otherwise, when used herein, the terms "imageable element", "negative-working lithographic printing precursor", and "lithographic printing precursor" are meant to be references to embodiments useful in the practice of the present invention.

The lithographic printing precursors can have any useful form and size or shape including but not limited to, lithographic printing plate precursors, lithographic printing cylinders, lithographic printing sleeves (both hollow or solid), and lithographic printing tapes (including flexible printing webs) that can be used to form lithographic printing members that can be used for lithographic printing. In the following description, the term "lithographic printing precursor" is intended to include all of these lithographic forms.

The term "photochromic compound" generically refers to compounds used in this invention that can be provided in a "colorless" form but upon exposure to UV radiation, become colored. Thus, the colorless form of the photochromic compound is used in the coloration solution or developer (processing solution), but it becomes colored when it is exposed to UV radiation.

The term "coloration fluid" refers to whatever aqueous solution is used to deliver the photochromic compound(s) to the imaged lithographic printing precursor. Thus, the coloration fluid can be an acidic or alkaline developer, or it can be a separate acidic or alkaline solution used after development.

In addition, unless the context indicates otherwise, the various components described herein such as "photochromic compound", "free radical polymerizable compound", "infrared radiation absorbing compound", "polymeric binder", and other components also refer to mixtures of such components. Thus, the use of the article "a" or "an" is not necessarily meant to refer to only a single component.

By "single-layer" lithographic printing precursors, we mean precursors that have only a single layer needed for providing an image. However, such precursors can comprise additional non-imaging layers on either side of the substrate or over the imageable layer.

By "multi-layer" lithographic printing precursors, we mean precursors that have at least two layers needed for providing an image. Such lithographic printing precursors are generally positive-working.

Unless otherwise indicated, percentages refer to percents by dry weight. Coating coverage refers to dry amounts.

For clarification of definitions for any terms relating to polymers, reference should be made to "Glossary of Basic Terms in Polymer Science" as published by the International Union of Pure and Applied Chemistry ("IUPAC"), *Pure Appl. Chem.* 68, 2287-2311 (1996). However, any definitions explicitly set forth herein should be regarded as controlling.

Unless otherwise indicated, the term "polymer" refers to high and low molecular weight polymers including oligomers and includes homopolymers and copolymers.

The term "copolymer" refers to polymers that are derived from two or more different monomers. That is, they comprise recurring units having at least two different chemical structures.

The term "backbone" refers to the chain of atoms in a polymer to which a plurality of pendant groups can be attached. An example of such a backbone is an "all carbon" backbone obtained from the polymerization of one or more ethylenically unsaturated polymerizable monomers. However, other backbones can include heteroatoms wherein the polymer is formed by a condensation reaction or some other means.

Photochromic Compounds

The color contrast obtained using the present invention is provided using the colorless, UV-sensitive photochromic compounds (dyes) described herein that can be converted to colored forms upon exposure to ultraviolet radiation so the imaged (exposed) regions areas become darkened. Where the image is not visible or measurable on the imaged precursor or was not easily read, the process of absorption and UV exposure produces a stable, visible, and readable or measurable image. The photochromic compounds can be pigments or dyes and in most instances, they are water-insoluble or have generally low water solubility. Thus, the photochromic compounds can be considered hydrophobic or oleophilic and because of this property, the compounds readily attach to the ink-acceptable surface of the imaged lithographic printing precursors and are generally repelled by hydrophilic regions in the imaged precursor when fountain solution is present.

Useful photochromic compounds undergo reversible photo-isomerization between two isomers with different absorption spectra upon irradiation with appropriate wavelength of light (UV). Photogenerated colored isomers, in general, can return to the initial colorless isomers either photochemically or thermally at room temperature under visible light. In other words, some photogenerated colored isomers are often unstable under room light at room temperature. The best photochromic compounds used in this invention are generally stable to visible light at room temperature for a desired period of time. Those compounds that are less stable can be used within a few minutes of mixing in solution. Those photochromic compounds with unstable color forms under visible light are less desirable for use in the present invention but they could be used in certain circumstances where long-term light stability is less important.

The most useful photochromic compounds are those having very low photo-decoloration quantum yields and are thermally stable at room temperature when exposed to 500 lumens of visible light (400 to 700 nm) for 100 hours. Desirable photochromic compounds have one or more electron donating groups attached to dithienethylene molecules and that these molecules are essentially colorless, but they readily give stable colored isomers under UV radiation at room temperature. Mixtures of photochromic compounds can be used if desired.

Some very useful photochromic compounds can be represented by the general Structure (I) shown below.

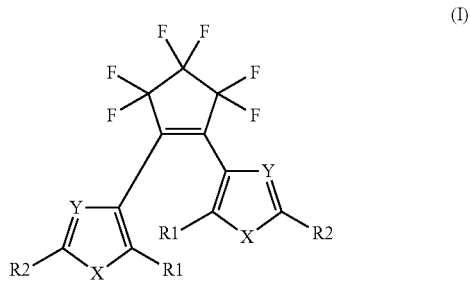

(I)

wherein X is oxygen, sulfur, sulfone, or a substituted or unsubstituted nitrogen (that is a mono- or dialkylamine, or mono- or diarylamine). In particular X is sulfur.

Y is oxygen or a substituted or substituted carbon atom. For example, the carbon can be substituted with an alkyl, cycloalkyl, or aryl group. Typically, Y is unsubstituted carbon.

$R^1$ is an electron donating group, and $R^2$ is hydrogen or any other substituent.

In particular, $R^1$ is an electron donating group including but not limited to, alkoxy groups having at least 2 carbon atoms, cycloalkoxy groups having at least 5 carbon atoms in the carbocyclic ring, and aryloxy groups having at least 6 carbon atoms in the carbocyclic ring. Other useful $R^1$ electron donating groups include but are not limited to:

—S—$R^3$ wherein $R^3$ is a substituted or unsubstituted alkyl group having 1 to 6 carbon atoms, substituted or unsubstituted cycloalkyl group having 5 to 8 carbon atoms in the hydrocarbon ring, substituted or unsubstituted aryl group having 6 or 10 carbon atoms in the aromatic carbocyclic ring, and —Z'($R^4$)($R^5$) wherein Z' is a nitrogen atom, and $R^4$ and $R^5$ are the same or different substituted or unsubstituted alkyl groups having 1 to 5 carbon atoms, or substituted or unsubstituted aryl groups such as substituted or unsubstituted phenyl or naphthyl groups. One, but not both of $R^4$ and $R^5$, can be hydrogen.

The $R^1$ groups can be the same or different in the two heterocyclic rings.

$R^2$ is hydrogen or an alkyl, aryl, cycloalkyl, alkoxy, cycloalkoxy, dialkylamino, or aryl group, or $R^2$ can be joined with the Y group on the same ring to form a fused ring system. The $R^2$ groups can be the same or different from each other and they can be the same or different from $R^1$. They can, for instance be hydrogen, substituted or unsubstituted alkyl groups having 1 to 5 carbon atoms, substituted or unsubstituted aryl groups (such as substituted or unsubstituted phenyl or naphthyl groups), substituted or unsubstituted heteroaryl groups having 5 to 8 carbon and heteroatoms in the ring (such as substituted or unsubstituted pyridyl groups), substituted or unsubstituted alkoxy groups having 1 to 6 carbon atoms, substituted or unsubstituted aryloxy groups as defined above for $R^1$, or substituted or unsubstituted amino groups (such as monoalkyl-, dialkyl-, monoaryl-, or diaryl-amino groups).

$R^2$ can also be joined together with the Y group on the same ring to form fused rings with the five-member heterocyclic rings.

It can be useful to incorporate water-solubilizing groups such as sulfonate, carboxy, and other anionic groups into the photochromic compound molecules in a suitable location, for example as substituents in alkyl or aryl groups. For example, water-solubilizing groups such as carboxylate or sulfonate groups can be present on phenyl or alkyl groups that are present as substituents, or as terminal groups on alkyl chains.

Photochromic compounds useful in the practice of this invention include, but not limited to, the following compounds:

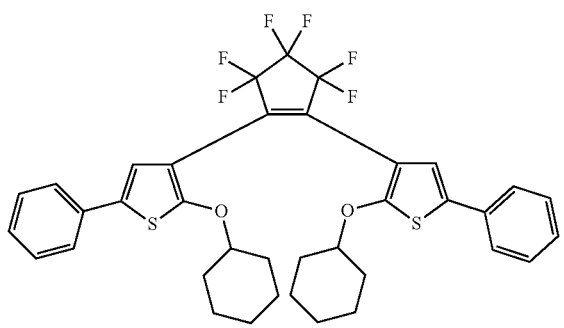

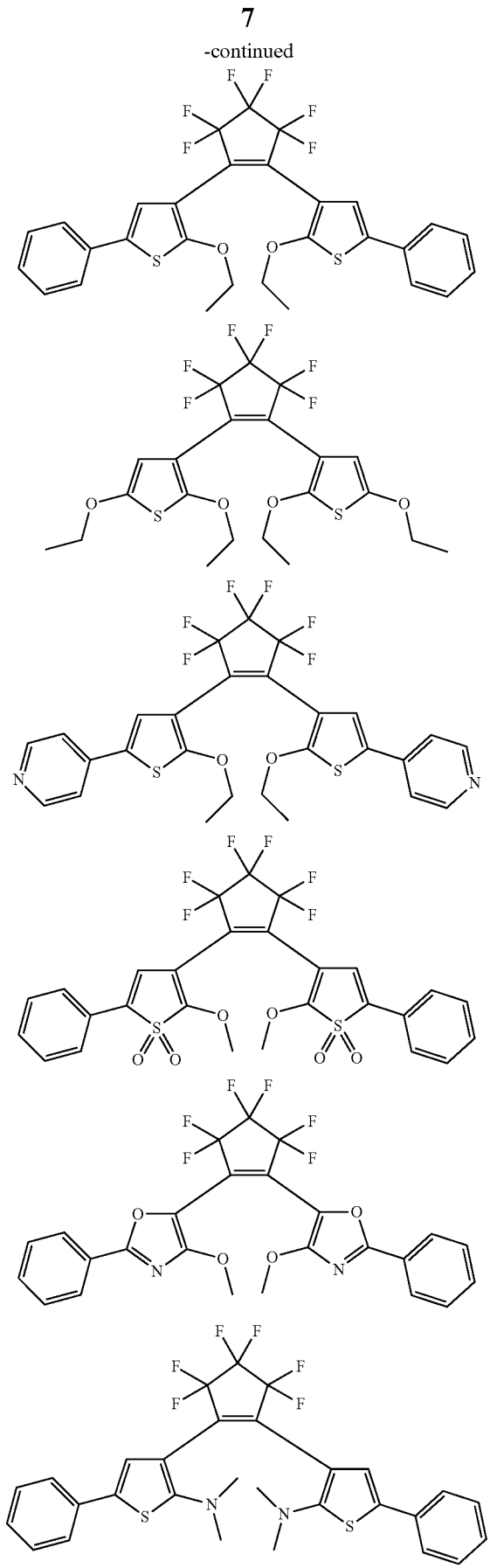

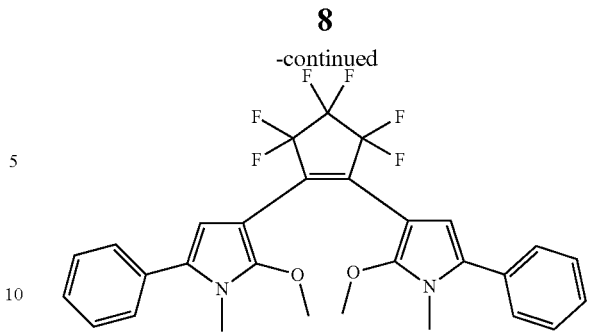

The photochromic compounds useful in the practice of this invention can be prepared using known starting materials and conditions, for example as described by Masahiro et al. in *J. Org. Chem.* 67, 2002, pp. 4574-78. A representative synthetic method is also shown below before the Examples.

The photochromic compounds can be introduced into a developing or processing liquid or into a separate coloration solution. More details of the use the compounds are provided below.

Many of the useful photochromic compounds are water-insoluble, but they can be dissolved in a suitable organic solvent and introduced into the developer or coloration solution in a manner such that it either remains in solution or is present in a very fine suspension or dispersion. Such organic solvents are described in more detail below and can be present in the coloration solution in an amount of from about 1 to about 25 weight % or typically from about 10 to about 20 weight %, of the total solution weight.

The photochromic compounds can be supplied in the coloration solution in which it is to be used, or it can be supplied in a separate solution that is mixed with the final coloration solution used by a customer. The photochromic compounds can also be supplied in solid or liquid form and mixed into the coloration solution when required, for example, just before their use. In all instances, the UV-sensitive photochromic compounds should be kept in light tight containers to avoid premature UV exposure and discoloration.

Negative-Working Lithographic Printing Precursors

The negative-working lithographic printing precursors used in this invention include a radiation-sensitive composition disposed on a suitable substrate to form an imageable layer that comprises a free radically polymerizable component, a free radical initiator composition, a radiation absorbing compound, and a polymeric binder. The radiation-sensitive composition (and imageable layer) includes one or more free radically polymerizable components, each of which contains one or more free radically polymerizable groups that can be polymerized using free radical initiation. For example, such free radically polymerizable components can contain one or more free radical polymerizable monomers or oligomers having one or more addition polymerizable ethylenically unsaturated groups, crosslinkable ethylenically unsaturated groups, ring-opening polymerizable groups, azido groups, aryldiazonium salt groups, aryldiazosulfonate groups, or a combination thereof. Similarly, crosslinkable polymers having such free radically polymerizable groups can also be used.

Suitable ethylenically unsaturated components that can be polymerized or crosslinked include ethylenically unsaturated polymerizable monomers that have one or more of the polymerizable groups, including unsaturated esters of alcohols, such as acrylate and methacrylate esters of polyols. Oligomers or prepolymers, such as urethane acrylates and methacrylates, epoxide acrylates and methacrylates, polyester acrylates and methacrylates, polyether acrylates and methacrylates, and unsaturated polyester resins can also be used. In some embodiments, the free radically polymerizable component comprises carboxy groups.

Useful free radically polymerizable components include free-radical polymerizable monomers or oligomers that comprise addition polymerizable ethylenically unsaturated groups including multiple acrylate and methacrylate groups and combinations thereof, or free-radical crosslinkable polymers. Free radically polymerizable compounds include those derived from urea urethane(meth)acrylates or urethane(meth) acrylates having multiple polymerizable groups. For example, a free radically polymerizable component can be prepared by reacting DESMODUR® N100 aliphatic polyisocyanate resin based on hexamethylene diisocyanate (Bayer Corp., Milford, Conn.) with hydroxyethyl acrylate and pentaerythritol triacrylate. Useful free radically polymerizable compounds include NK Ester A-DPH (dipentaerythritol hexaacrylate) that is available from Kowa American, and Sartomer 399 (dipentaerythritol pentaacrylate), Sartomer 355 (di-trimethylolpropane tetraacrylate), Sartomer 295 (pentaerythritol tetraacrylate), and Sartomer 415 [ethoxylated (20) trimethylolpropane triacrylate] that are available from Sartomer Company, Inc.

Also useful are urea urethane(meth)acrylates and urethane (meth)acrylates as described in U.S. Pat. No. 6,582,882 (Pappas et al.), U.S. Pat. No. 6,899,994 (noted above), and U.S. Pat. No. 7,153,632 (Saraiya et al.) and WO 2007/077207, all of which are incorporated herein by reference.

Numerous other free radically polymerizable components are known to those skilled in the art and are described in considerable literature including *Photoreactive Polymers: The Science and Technology of Resists*, A Reiser, Wiley, New York, 1989, pp. 102-177, by B. M. Monroe in *Radiation Curing: Science and Technology*, S. P. Pappas, Ed., Plenum, New York, 1992, pp. 399-440, and in "Polymer Imaging" by A. B. Cohen and P. Walker, in *Imaging Processes and Material*, J. M. Sturge et al. (Eds.), Van Nostrand Reinhold, New York, 1989, pp. 226-262. For example, useful free radically polymerizable components are also described in EP 1,182,033A1 (noted above), beginning with paragraph [0170], and in U.S. Pat. No. 6,309,792 (Hauck et al.), U.S. Pat. No. 6,569,603 (Furukawa), and U.S. Pat. No. 6,893,797 (Munnelly et al.).

In addition to, or in place of the free radically polymerizable components described above, the radiation-sensitive composition can include polymeric materials that include side chains attached to the backbone, which side chains include one or more free radically polymerizable groups (such as ethylenically unsaturated groups) that can be polymerized (crosslinked) in response to free radicals produced by the initiator composition (described below). There can be at least two of these side chains per molecule. The free radically polymerizable groups (or ethylenically unsaturated groups) can be part of aliphatic or aromatic acrylate side chains attached to the polymeric backbone. Generally, there are at least 2 and up to 20 such groups per molecule, or typically from 2 to 10 such groups per molecule.

Such free radically polymerizable polymers can also comprise hydrophilic groups including but not limited to, carboxy, sulfo, or phospho groups, either attached directly to the backbone or attached as part of side chains other than the free radically polymerizable side chains.

Useful commercial products that comprise polymers that can be used in this manner include Bayhydrol® UV VP LS 2280, Bayhydrol® UV VP LS 2282, Bayhydrol® UV VP LS 2317, Bayhydrol® UV VP LS 2348, and Bayhydrol® UV XP 2420, that are all available from Bayer MaterialScience, as well as Laromer™ LR 8949, Laromer™ LR 8983, and Laromer™ LR 9005, that are all available from BASF.

The free radically polymerizable component can be present in the radiation-sensitive composition in an amount sufficient to render the composition insoluble in an aqueous developer after exposure to radiation. This is generally from about 10 to about 70 weight % and typically from about 20 to about 50 weight % based on the dry weight of the radiation-sensitive composition.

The radiation-sensitive composition can also include an initiator composition containing one or more free radical initiators that are capable of generating radicals sufficient to initiate polymerization of the radically polymerizable component upon exposure to the appropriate imaging radiation. The initiator composition can be responsive, for example, to electromagnetic radiation in the infrared spectral regions, corresponding to the broad spectral range of from about 700 nm to about 1400 nm, and typically from about 700 nm to about 1200 nm. Alternatively, the initiator composition can be responsive to exposing radiation in the violet region of from about 250 to about 450 nm and typically from about 300 to about 450 nm.

There are numerous compounds known in the literature that can be used in this manner including but not limited to, organic boron salts, s-triazines, benzoyl-substituted compounds, onium salts (such as iodonium, sulfonium, diazonium, and phosphonium salts), trihaloalkyl-substituted compounds, metallocenes (such as titanocenes), ketoximes, thio compounds, organic peroxides, or a combination of two or more of these compounds. Hexaarylbiimidazoles, onium compounds, and thiol compounds as well as mixtures of two or more thereof are desired coinitiators or free radical generators, and especially hexaarylbiimidazoles and mixtures thereof with thiol compounds are useful.

Suitable hexaarylbiimidazoles are for example described in U.S. Pat. No. 4,565,769 (Dueber et al.) and U.S. Pat. No. 3,445,232 (Shirey) and can be prepared according to known methods, such as the oxidative dimerization of triarylimidazoles.

Other suitable initiator compositions comprise free radical initiators that include but are not limited to, amines (such as alkanol amines), thiol compounds, N-phenyl glycine and derivatives thereof, N,N-dialkylaminobenzoic acid esters, N-arylglycines and derivatives thereof (such as N-phenylglycine), aromatic sulfonylhalides, trihalogenomethylsulfones, imides (such as N-benzoyloxyphthalimide), diazosulfonates, 9,10-dihydroanthracene derivatives, N-aryl, S-aryl, or O-aryl polycarboxylic acids with at least 2 carboxy groups of which at least one is bonded to the nitrogen, oxygen, or sulfur atom of the aryl moiety, "co-initiators" described in U.S. Pat. No. 5,629,354 (West et al.), oxime ethers and oxime esters (such as those derived from benzoin), α-hydroxy or α-amino-acetophenones, alkyltriarylborates, trihalogenomethylarylsulfones, benzoin ethers and esters, peroxides (such as benzoyl peroxide), hydroperoxides (such as cumyl hydroperoxide), azo compounds (such as azo bis-isobutyronitrile) as described for example in U.S. Pat. No. 4,565,769 (Dueber et al.), borate and organoborate salts such as those described in U.S. Pat. No. 6,562,543 (Ogata et al.), and onium salts (such as ammonium salts, diaryliodonium salts, triarylsulfonium salts, aryldiazonium salts, and N-alkoxypyridinium salts). Other known initiator composition components are described for example in U.S. Patent Application Publication 2003/0064318 (Huang et al.).

IR-radiation sensitive initiator compositions generally comprise a free radical initiator that is an onium salt including but not limited to, a sulfonium, oxysulfoxonium, oxysulfonium, sulfoxonium, ammonium, selenonium, arsonium, phosphonium, diazonium, or halonium salt. Further details of useful onium salts, including representative examples, are provided in U.S. Patent Application Publication 2002/0068241 (Oohashi et al.), WO 2004/101280 (Munnelly et al.), and U.S. Pat. No. 5,086,086 (Brown-Wensley et al.), U.S. Pat. No. 5,965,319 (Kobayashi), U.S. Pat. No. 6,051,366 (Baumann et al.), and U.S. Pat. No. 7,368,215 (Munnelly et al.). For example, suitable phosphonium salts include positive-charged hypervalent phosphorus atoms with four organic substituents. Suitable sulfonium salts such as triphenylsulfonium salts include a positively-charged hypervalent sulfur with three organic substituents. Suitable diazonium salts possess a positive-charged azo group (that is —N=N+). Suitable ammonium salts include a positively-charged nitrogen atom such as substituted quaternary ammonium salts with four organic substituents, and quaternary nitrogen heterocyclic rings such as N-alkoxypyridinium salts. Suitable halonium salts include a positively-charged hypervalent halogen atom with two organic substituents. The onium salts generally include a suitable number of negatively-charged counterions such as halides, hexafluorophosphate, thiosulfate, hexafluoroantimonate, tetrafluoroborate, sulfonates, hydroxide, perchlorate, n-butyltriphenyl borate, tetraphenyl borate, and others readily apparent to one skilled in the art.

Useful halonium salts such as iodonium salts include an onium salt having a positively-charged iodonium, (4-methylphenyl)[4-(2-methylpropyl)phenyl]-moiety and a suitable negatively charged counterion. A representative example of such an iodonium salt is available as Irgacure® 250 from Ciba Specialty Chemicals (Tarrytown, N.Y.) that is (4-methylphenyl)[4-(2-methylpropyl)phenyl]iodonium hexafluorophosphate and is supplied in a 75% propylene carbonate solution.

Some useful boron components include organic boron salts that include an organic boron anion such as those described in U.S. Pat. No. 6,569,603 (noted above) that is paired with a suitable cation such as an alkali metal ion, an onium, or a cationic sensitizing dye. Useful onium cations include but are not limited to, ammonium, sulfonium, phosphonium, iodonium, and diazonium cations. Iodonium salts and particularly iodonium borates are particularly useful as initiator compounds in radiation-sensitive compounds that are designed for "on-press" development (described in more detail below). These particular free radical initiators can be used alone or in combination with co-initiators such as heterocyclic mercapto compounds including mercaptotriazoles, mercaptobenzimidazoles, mercaptobenzoxazoles, mercaptobenzothiazoles, mercaptobenzoxadiazoles, mercaptotetrazoles, such as those described for example in U.S. Pat. No. 6,884,568 (Timpe et al.) in amounts of at least 0.5 and up to and including 10 weight % based on the total solids of the IR radiation-sensitive composition. Useful mercaptotriazoles include 3-mercapto-1,2,4-triazole, 4-methyl-3-mercapto-1,2,4-triazole, 5-mercapto-1-phenyl-1,2,4-triazole, 4-amino-3-mercapto-1,2,4,-triazole, 3-mercapto-1,5-diphenyl-1,2,4-triazole, and 5-(p-aminophenyl)-3-mercapto-1,2,4-triazole.

Useful IR radiation-sensitive initiator compositions can comprise one or more diaryliodonium borate compounds as free radical initiators, each of which is represented by the following Structure (II):

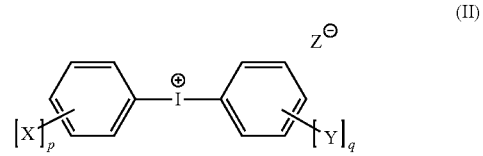

wherein X and Y are independently halo groups (for example, fluoro, chloro, or bromo), substituted or unsubstituted alkyl groups having 1 to 20 carbon atoms (for example, methyl, chloromethyl, ethyl, 2-methoxyethyl, n-propyl, isopropyl, isobutyl, n-butyl, t-butyl, all branched and linear pentyl groups, 1-ethylpentyl, 4-methylpentyl, all hexyl isomers, all octyl isomers, benzyl, 4-methoxybenzyl, p-methylbenzyl, all dodecyl isomers, all icosyl isomers, and substituted or unsubstituted mono- and poly-, branched and linear haloalkyls), substituted or unsubstituted alkyloxy having 1 to 20 carbon atoms (for example, substituted or unsubstituted methoxy, ethoxy, iso-propoxy, t-butoxy, (2-hydroxytetradecyl)oxy, and various other linear and branched alkyleneoxyalkoxy groups), substituted or unsubstituted aryl groups having 6 or 10 carbon atoms in the carbocyclic aromatic ring (such as substituted or unsubstituted phenyl and naphthyl groups including mono- and polyhalophenyl and naphthyl groups), or substituted or unsubstituted cycloalkyl groups having 3 to 8 carbon atoms in the ring structure (for example, substituted or unsubstituted cyclopropyl, cyclopentyl, cyclohexyl, 4-methylcyclohexyl, and cyclooctyl groups). For example, X and Y are independently substituted or unsubstituted alkyl groups having 1 to 8 carbon atoms, alkyloxy groups having 1 to 8 carbon atoms, or cycloalkyl groups having 5 or 6 carbon atoms in the ring, and more preferably, X and Y are independently substituted or unsubstituted alkyl groups having 3 to 6 carbon atoms (and particularly branched alkyl groups having 3 to 6 carbon atoms). Thus, X and Y can be the same or different groups, the various X groups can be the same or different groups, and the various Y groups can be the same or different groups. Both "symmetric" and "asymmetric" diaryliodonium borate compounds are contemplated by this invention but the "symmetric" compounds are useful (that is, they have the same groups on both phenyl rings). Thus, it is understood that the carbon atoms in the phenyl rings that are not substituted by X or Y groups have a hydrogen atom at those ring positions.

Z⁻ is an organic borate anion represented by the following Structure (III):

wherein $R_1$, $R_2$, $R_3$, and $R_4$ are independently substituted or unsubstituted alkyl groups having 1 to 12 carbon atoms (such as methyl, ethyl, n-propyl, iso-propyl, n-butyl, isobutyl, t-butyl, all pentyl isomers, 2-methylpentyl, all hexyl isomers, 2-ethylhexyl, all octyl isomers, 2,4,4-trimethylpentyl, all nonyl isomers, all decyl isomers, all undecyl isomers, all dodecyl isomers, methoxymethyl, and benzyl) other than fluoroalkyl groups, substituted or unsubstituted carbocyclic aryl groups having 6 to 10 carbon atoms in the aromatic ring (such as phenyl, p-methylphenyl, 2,4-methoxyphenyl, naphthyl, and pentafluorophenyl groups), substituted or unsubstituted alkenyl groups having 2 to 12 carbon atoms (such as ethenyl, 2-methylethenyl, allyl, vinylbenzyl, acryloyl, and crotonotyl groups), substituted or unsubstituted alkynyl groups having 2 to 12 carbon atoms (such as ethynyl, 2-methylethynyl, and 2,3-propynyl groups), substituted or unsubstituted cycloalkyl groups having 3 to 8 carbon atoms in the ring structure (such as cyclopropyl, cyclopentyl, cyclohexyl, 4-methylcyclohexyl, and cyclooctyl groups), or substituted or unsubstituted heterocyclyl groups having 5 to 10 carbon, oxygen, sulfur, and nitrogen atoms (including both aromatic and non-aromatic groups, such as substituted or unsubstituted pyridyl, pyrimidyl, furanyl, pyrrolyl, imidazolyl, triazolyl, tetrazoylyl, indolyl, quinolinyl, oxadiazolyl, and benzoxazolyl groups). Alternatively, two or more of $R_1$, $R_2$, $R_3$, and $R_4$ can be joined together to form a heterocyclic ring with the boron atom, such rings having up to 7 carbon, nitrogen, oxygen, or nitrogen atoms.

For example, $R_1$, $R_2$, $R_3$, and $R_4$ for Structure (III) are independently substituted or unsubstituted alkyl or aryl groups as defined above, or at least 3 of $R_1$, $R_2$, $R_3$, and $R_4$ are the same or different substituted or unsubstituted aryl groups (such as substituted or unsubstituted phenyl groups). In some embodiments, all of $R_1$, $R_2$, $R_3$, and $R_4$ are the same or different substituted or unsubstituted aryl groups or, all of the groups are the same substituted or unsubstituted phenyl group. For example, $Z^-$ is a tetraphenyl borate wherein the phenyl groups are substituted or unsubstituted.

Representative iodonium borate compounds useful in this invention include but are not limited to, 4-octyloxyphenyl phenyliodonium tetraphenylborate, [4-[(2-hydroxytetradecyl)-oxy]phenyl]phenyliodonium tetraphenylborate, bis(4-t-butylphenyl)iodonium tetraphenylborate, 4-methylphenyl-4'-hexylphenyliodonium tetraphenylborate, 4-methylphenyl-4'-cyclohexylphenyliodonium tetraphenylborate, bis(t-butylphenyl)iodonium tetrakis(pentafluorophenyl)borate, 4-hexylphenyl-phenyliodonium tetraphenylborate, 4-methylphenyl-4'-cyclohexylphenyliodonium n-butyltriphenylborate, 4-cyclohexylphenyl-phenyliodonium tetraphenylborate, 2-methyl-4-t-butylphenyl-4'-methylphenyliodonium tetraphenylborate, 4-methylphenyl-4'-pentylphenyliodonium tetrakis[3,5-bis(trifluoromethyl)phenyl]borate, 4-methoxyphenyl-4'-cyclohexylphenyliodonium tetrakis (penta-fluorophenyl)borate, 4-methylphenyl-4'-dodecylphenyliodonium tetrakis(4-fluorophenyl)borate, bis(dodecylphenyl)iodonium tetrakis(pentafluorophenyl)borate, and bis(4-t-butylphenyl)iodonium tetrakis(1-imidazolyl)borate. Useful compounds include bis(4-t-butylphenyl)iodonium tetraphenylborate, 4-methylphenyl-4'-hexylphenyliodonium tetraphenylborate, 2-methyl-4-t-butylphenyl-4'-methylphenyliodonium tetraphenylborate, and 4-methylphenyl-4'-cyclohexylphenyliodonium tetraphenylborate. Mixtures of two or more of these compounds can also be used in the initiator composition.

The initiator composition includes one or more free radical initiators that are generally present in the radiation-sensitive composition in an amount of from about 0.5% to about 30% (or typically from about 2 weight % to about 20 weight %), based on the total solids of the radiation-sensitive composition or the dry weight of the coated imageable layer. The optimum amount of the various initiator components can differ for various compounds and the sensitivity of the radiation-sensitive composition that is desired and would be readily apparent to one skilled in the art.

One or more co-initiators can be used generally in an amount of from about 0.2 to about 25 wt. %, or typically from about 0.5 to about 15 wt. %, based on the dry layer weight.

In some embodiments, the radiation-sensitive composition contains a UV sensitizer where the free-radical generating compound is UV radiation sensitive (that is at least 150 nm and up to and including 475 nm), thereby facilitating photopolymerization. In some other embodiments, the radiation sensitive compositions are sensitized to "violet" radiation in the range of at least 375 nm and up to and including 475 nm. Useful sensitizers for such compositions include certain pyrilium and thiopyrilium dyes and 3-ketocoumarins. Some other useful sensitizers for such spectral sensitivity are described for example, in U.S. Pat. No. 6,908,726 (Korionoff et al.), WO 2004/074929 (Baumann et al.) that describes useful bisoxazole derivatives and analogues, and U.S. Patent Application Publications 2006/0063101 and 2006/0234155 (both Baumann et al.) all incorporated herein by reference.

Still other useful sensitizers are the oligomeric or polymeric compounds having Structure (I) units defined in WO 2006/053689 (Strehmel et al.) that have a suitable aromatic or heteroaromatic unit that provides a conjugated π-system between two heteroatoms.

Additional useful "violet"-visible radiation sensitizers are the compounds described in WO 2004/074929 (Baumann et al.). These compounds comprise the same or different aromatic heterocyclic groups connected with a spacer moiety that comprises at least one carbon-carbon double bond that is conjugated to the aromatic heterocyclic groups, and are represented in more detail by Formula (I) in the noted publication.

Other useful sensitizers for the violet region of sensitization are the 2,4,5-triaryloxazole derivatives as described in WO 2004/074930 (Baumann et al.) that is incorporated herein by reference. These compounds can be used alone or with a co-initiator as described above. Useful 2,4,5-triaryloxazole derivatives can be represented by the Structure $G-(Ar_1)_3$ wherein $Ar_1$ is the same or different, substituted or unsubstituted carbocyclic aryl group having 6 to 12 carbon atoms in the ring, and G is a furan or oxazole ring, or the Structure $G-(Ar_1)_2$ wherein G is an oxadiazole ring.

Still another class of useful violet radiation sensitizers includes compounds represented by the Structure $Ar_1-G-Ar_2$ wherein $Ar_1$ and $Ar_2$ are the same or different substituted or unsubstituted aryl groups having 6 to 12 carbon atoms in the ring, or $Ar_2$ can be an arylene-$G-Ar_1$ or arylene-$G-Ar_2$ group, and G is a furan, oxazole, or oxadiazole ring. $Ar_1$ is the same as defined above, and $Ar_2$ can be the same or different aryl group as $Ar_1$. "Arylene" can be any of the aryl groups defined for $Ar_1$ but with a hydrogen atom removed to render them divalent in nature.

IR radiation-sensitive sensitivity for the radiation-sensitive composition can be provided by the presence of one or more infrared radiation absorbing compounds, chromophores, or sensitizers that absorb imaging radiation, or sensitize the composition to imaging infrared radiation having a $\lambda_{max}$ of from about 700 nm and up to and including 1400 nm, and typically from about 700 to about 1200 nm.

Useful IR radiation absorbing chromophores include various IR-sensitive dyes ("IR dyes"). Examples of suitable IR dyes comprising the desired chromophore include but are not limited to, azo dyes, squarilium dyes, croconate dyes, triarylamine dyes, thioazolium dyes, indolium dyes, oxonol dyes, oxaxolium dyes, cyanine dyes, merocyanine dyes, phthalocyanine dyes, indocyanine dyes, indotricarbocyanine dyes, oxatricarbocyanine dyes, thiocyanine dyes, thiatricarbocyanine dyes, merocyanine dyes, cryptocyanine dyes, naphthalocyanine dyes, polyaniline dyes, polypyrrole dyes, polythiophene dyes, chalcogenopyryloarylidene and bi(chalcogenopyrylo)polymethine dyes, oxyindolizine dyes, pyrylium dyes, pyrazoline azo dyes, oxazine dyes, naphthoquinone dyes, anthraquinone dyes, quinoneimine dyes, methine dyes, arylmethine dyes, squarine dyes, oxazole dyes, croconine dyes, porphyrin dyes, and any substituted or ionic form of the preceding dye classes. Suitable dyes are also described in U.S. Pat. No. 5,208,135 (Patel et al.), U.S. Pat. No. 6,153,356 (Urano et al.), U.S. Pat. No. 6,264,920 (Achilefu et al.), U.S. Pat. No. 6,309,792 (Hauck et al.), U.S. Pat. No. 6,569,603 (noted above), U.S. Pat. No. 6,787,281 (Tao et al.), U.S. Pat. No. 7,135,271 (Kawaushi et al.), and EP 1,182, 033A2 (noted above). Infrared radiation absorbing N-alkylsulfate cyanine dyes are described for example in U.S. Pat. No. 7,018,775 (Tao). A general description of one class of suitable cyanine dyes is shown by the formula in paragraph [0026] of WO 2004/101280 (Munnelly et al.).

In addition to low molecular weight IR-absorbing dyes, IR dye chromophores bonded to polymers can be used as well. Moreover, IR dye cations can be used as well, that is, the cation is the IR absorbing portion of the dye salt that ionically interacts with a polymer comprising carboxy, sulfo, phospho, or phosphono groups in the side chains.

Near infrared absorbing cyanine dyes are also useful and are described for example in U.S. Pat. No. 6,309,792 (noted above), U.S. Pat. No. 6,264,920 (Achilefu et al.), U.S. Pat. No. 6,153,356 (noted above), and U.S. Pat. No. 5,496,903 (Watanate et al.). Suitable dyes can be formed using conventional methods and starting materials or obtained from various commercial sources including American Dye Source (Baie D'Urfe, Quebec, Canada) and FEW Chemicals (Germany). Other useful dyes for near infrared diode laser beams are described, for example, in U.S. Pat. No. 4,973,572 (DeBoer).

Still other useful infrared radiation absorbing compounds are copolymers can comprise covalently attached ammonium, sulfonium, phosphonium, or iodonium cations and infrared radiation absorbing cyanine anions that have two or four sulfonate or sulfate groups, or infrared radiation absorbing oxonol anions, as described for example in U.S. Pat. No. 7,049,046 (Tao et al.).

The radiation absorbing compounds (or sensitizers) can be present in the radiation sensitive composition (or imageable layer) in an amount generally of at least 1% and up to and including 30% and typically at least 3 and up to and including 20%, based on total solids in the composition, that also corresponds to the total dry weight of the imageable layer. The particular amount needed for this purpose would be readily apparent to a skilled worker in the art.

The radiation-sensitive composition includes one or more polymeric binders that are generally used for off-press developability include any alkaline solution soluble (or dispersible) polymer having an acid value of from about 20 to about 400. The following described polymeric binders are particularly useful in the manner but this is not an exhaustive list:

I. Polymers formed by polymerization of a combination or mixture of (a) (meth)acrylonitrile, (b) poly(alkylene oxide) esters of (meth)acrylic acid, and optionally (c) (meth)acrylic acid, (meth)acrylate esters, styrene and its derivatives, and (meth)acrylamide as described for example in U.S. Pat. No. 7,326,521 (Tao et al.) that is incorporated herein by reference. Some particularly useful polymeric binders in this class are derived from one or more (meth)acrylic acids, (meth)acrylate esters, styrene and its derivatives, vinyl carbazoles, and poly (alkylene oxide) (meth)acrylates.

II. Polymers having pendant allyl ester groups as described in U.S. Pat. No. 7,332,253 (Tao et al.) that is incorporated herein by reference. Such polymers may also include pendant cyano groups or have recurring units derived from a variety of other monomers as described in Col. 8, line 31 to Col. 10, line 3 of the noted patent.

III. Polymers having all carbon backbones wherein at least 40 and up to 100 mol % (and typically from about 40 to about 50 mol %) of the carbon atoms forming the all carbon backbones are tertiary carbon atoms, and the remaining carbon atoms in the all carbon backbone being non-tertiary carbon atoms. By "tertiary carbon", we refer to a carbon atom in the all carbon backbone that has three valences filled with radicals or atoms other than a hydrogen atom (which fills the fourth valence). By "non-tertiary carbon", we mean a carbon atom in the all carbon backbone that is a secondary carbon (having two valences filled with hydrogen atoms) or a quaternary carbon (having no hydrogen atoms attached). Typically, most of the non-tertiary carbon atoms are secondary carbon atoms. One way to represent a tertiary carbon atom in the all carbon backbone is with the following Structure (T-CARBON):

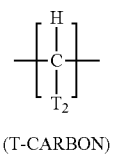

(T-CARBON)

wherein $T_2$ is a group other than hydrogen provided that $T_2$ does not include an ethylenically unsaturated free radically reactive group (such as a —C=C— group). In many embodiments, $T_2$ is a pendant group selected from N-carbazole, aryl (defined similarly as for Ar below), halo, cyano, —C(=O)R, —C(=O)Ar, —C(=O)OR, —C(=O)OAr, —C(=O)NHR, and —C(=O)NHAr pendant groups, wherein R is hydrogen or an alkyl, cycloalkyl, halo, alkoxy, acyl, or acyloxy group, and Ar is an aryl group other than a styryl group. The quaternary carbon atoms present in the all carbon backbone of the polymeric binder can also have the same or different pendant groups filling two of the valences. For example, one or both valences can be filled with the same or different alkyl groups as defined above for R, or one valence can be filled with an alkyl group and another valence can be filled with a N-carbazole, aryl other than a styryl group, halo, cyano, —C(=O)R, —C(=O)Ar, —C(=O)OR, —C(=O)OAr, —C(=O)NHR, or —C(=O)NHAr pendant group, wherein R and Ar are as defined above. The pendant groups attached to the tertiary and quaternary carbons in the all carbon backbone can be the same or different and typically, they are different. It should also be understood that the pendant groups attached to the various tertiary carbon atoms can be the same throughout the polymeric molecule, or they can be different. For example, the tertiary carbon atoms can be derived from the same or different ethylenically unsaturated polymerizable monomers. Moreover, the quaternary carbon atoms throughout the polymeric molecule can have the same or different pendant groups.

These polymeric binders are defined in more detail in U.S. Patent Application Publication 2008-0280229 (Tao et al.) that is incorporated herein by reference.

IV. Polymeric binders that have one or more ethylenically unsaturated pendant groups (reactive vinyl groups) attached to the polymer backbone. Such reactive groups are capable of undergoing polymerizable or crosslinking in the presence of free radicals. The pendant groups can be directly attached to the polymer backbone with a carbon-carbon direct bond, or through a linking group ("X") that is not particularly limited. The reactive vinyl groups may be substituted with at least one halogen atom, carboxy group, nitro group, cyano group, amide group, or alkyl, aryl, alkoxy, or aryloxy group, and particularly one or more alkyl groups. In some embodiments, the reactive vinyl group is attached to the polymer backbone through a phenylene group as described, for example, in U.S. Pat. No. 6,569,603 (Furukawa et al.) that is incorporated herein by reference. Other useful polymeric binders have vinyl groups in pendant groups that are described, for example in EP 1,182,033A1 (Fujimaki et al.) and U.S. Pat. No. 4,874,686 (Urabe et al.), U.S. Pat. No. 7,729,255 (Tao et al.), U.S. Pat. No. 6,916,595 (Fujimaki et al.), and U.S. Pat. No. 7,041,416 (Wakata et al.) that are incorporated by reference, especially with respect to the general formulae (1) through (3) noted in EP 1,182,033A1.

V. Polymeric binders can have pendant 1H-tetrazole groups as described in U.S. Patent Application Publication 2009-0142695 (Baumann et al.) that is incorporated herein by reference.

VI. Still other useful polymeric binders may be homogenous, that is, dissolved in the coating solvent, or may exist as discrete particles and include but are not limited to, (meth) acrylic acid and acid ester resins [such as (meth)acrylates], polyvinyl acetals, phenolic resins, polymers derived from styrene, N-substituted cyclic imides or maleic anhydrides, such as those described in EP 1,182,033 (noted above) and U.S. Pat. No. 6,309,792 (Hauck et al.), U.S. Pat. No. 6,352,812 (Shimazu et al.), U.S. Pat. No. 6,569,603 (noted above), and U.S. Pat. No. 6,893,797 (Munnelly et al.). Also useful are the vinyl carbazole polymers described in U.S. Pat. No. 7,175,949 (Tao et al.). Other useful polymeric binders are particulate poly(urethane-acrylic) hybrids that are distributed (usually uniformly) throughout the imageable layer. Each of these hybrids has a molecular weight of from about 50,000 to about 500,000 and the particles have an average particle size of from about 10 to about 10,000 nm (typically from about 30 to about 500 nm).

The polymeric binder is generally present in the radiation-sensitive composition (and imageable layer) in an amount of at least 2.5 and up to 70 weight %, and typically from about 10 to about 50 weight % based on the total solids in the composition and layer.

The radiation-sensitive composition (and imageable layer) can also include a variety of optional compounds including but not limited to, dispersing agents, humectants, biocides, plasticizers, surfactants for coatability or other properties, viscosity builders, contrast dyes or colorants other than those described above (such as crystal violet, methyl violet, ethyl violet, Victoria Blue B, Victoria Blue R, malachite green, and brilliant green), pH adjusters, drying agents, defoamers, preservatives, antioxidants, color developers, development aids, rheology modifiers or combinations thereof, or any other addenda commonly used in the lithographic art, in conventional amounts. Useful viscosity builders include hydroxypropyl cellulose, hydroxyethyl cellulose, carboxymethyl cellulose, and poly(vinyl pyrrolidones).

Additional additives to the imageable layer include color developers or acidic compounds. As color developers, we mean to include monomeric phenolic compounds, organic acids or metal salts thereof, oxybenzoic acid esters, acid clays, and other compounds described for example in U.S. Patent Application Publication 2005/0170282 (Inno et al.). Specific examples of phenolic compounds include but are not limited to, 2,4-dihydroxybenzophenone, 4,4'-isopropylidene-diephenol (Bisphenol A), p-t-butylphenol, 2,4,-dinitrophenol, 3,4-dichlorophenol, 4,4'-methylene-bis(2,6'-di-t-butylphenol), p-phenylphenol, 1,1-bis(4-hydroxyphenyl) cyclohexane, 1,1-bis(4-hydroxyphenyl)-2-ethylhexene, 2,2-bis(4-hydroxyphenyl)butane, 2,2'-methylenebis(4-t-butylphenol), 2,2'-methylenebis($\alpha$-phenyl-p-cresol) thiodiphenol, 4,4'-thiobis(6-t-butyl-m-cresol) sulfonyldiphenol, p-butylphenol-formalin condensate, and p-phenylphenol-formalin condensate. Examples of useful organic acids or salts thereof include but are not limited to, phthalic acid, phthalic anhydride, maleic acid, benzoic acid, gallic acid, o-toluic acid, p-toluic acid, salicylic, 3-t-butylsalicylic, 3,5-di-3-t-butylsalicylic acid, 5-$\alpha$-methylbenzylsalicylic acid, 3,5-bis($\alpha$-methylbenzyl)salicylic acid, 3-t-octylsalicylic acid, and their zinc, lead, aluminum, magnesium, and nickel salts. Examples of the oxybenzoic acid esters include but are not limited to, ethyl p-oxybenzoate, butyl p-oxybenzoate, heptyl p-oxybenzoate, and benzyl p-oxybenzoate. Such color developers can be present in an amount of from about 0.5 to about 5 weight %, based on total imageable layer dry weight.

The radiation-sensitive composition (imageable layer) can further comprise one or more phosphate(meth)acrylates, each of which has a molecular weight generally greater than 200 and typically at least 300 and up to and including 1000. By "phosphate(meth)acrylate" we also mean to include "phosphate methacrylates" and other derivatives having substituents on the vinyl group in the acrylate moiety. Such compounds and their use in imageable layers are described in more detail in U.S. Pat. No. 7,175,969 (Ray et al.) that is incorporated herein by reference. The phosphate(meth)acrylate can be present in the radiation-sensitive composition in an amount of at least 0.5 and up to and including 20%, based on total dry composition weight.

The negative-working lithographic printing precursors can be formed by suitable application of a radiation-sensitive composition as described above to a suitable substrate to form an imageable layer. This substrate can be treated or coated in various ways as described below prior to application of the radiation-sensitive composition to improve hydrophilicity. Typically, there is only a single imageable layer comprising the radiation-sensitive composition. If the substrate has been treated to provide an "interlayer" for improved adhesion or hydrophilicity, the applied imageable layer is disposed thereon but these interlayers are not considered "imageable layers".

In most embodiments, the imageable layer is the outermost layer of the lithographic printing plate precursor.

The substrate generally has a hydrophilic surface, or at least a surface that is more hydrophilic than the applied imageable layer on the imaging side. The substrate comprises a support that can be composed of any material that is conventionally used to prepare imageable elements such as lithographic printing plates. It is usually in the form of a sheet, film, or foil (or web), and is strong, stable, and flexible and resistant to dimensional change under conditions of use so that color records will register a full-color image. Typically, the support can be any self-supporting material including polymeric films (such as polyester, polyethylene, polycarbonate, cellulose ester polymer, and polystyrene films), glass, ceramics, metal sheets or foils, or stiff papers (including resin-coated and metallized papers), or a lamination of any of these materials (such as a lamination of an aluminum foil onto a polyester film). Metal supports include sheets or foils of aluminum, copper, zinc, titanium, and alloys thereof.

Polymeric film supports can be modified on one or both flat surfaces with a "subbing" layer to enhance hydrophilicity, or paper supports can be similarly coated to enhance planarity. Examples of subbing layer materials include but are not limited to, alkoxysilanes, amino-propyltriethoxysilanes, glycidioxypropyl-triethoxysilanes, and epoxy functional polymers, as well as conventional hydrophilic subbing materials used in silver halide photographic films (such as gelatin and other naturally occurring and synthetic hydrophilic colloids and vinyl polymers including vinylidene chloride copolymers).

One useful substrate is composed of an aluminum support that can be treated using techniques known in the art, including roughening of some type by physical (mechanical) graining, electrochemical graining, or chemical graining, usually followed by acid anodizing. The aluminum support can be roughened by physical or electrochemical graining and then anodized using phosphoric or sulfuric acid and conventional procedures. A useful hydrophilic lithographic substrate is an electrochemically grained and sulfuric acid or phosphoric acid anodized aluminum support that provides a hydrophilic surface for lithographic printing.

Sulfuric acid anodization of the aluminum support generally provides an oxide weight (coverage) on the surface of from about 1.5 to about 5 g/m$^2$ and more typically from about 3 to about 4.3 g/m$^2$. Phosphoric acid anodization generally provides an oxide weight on the surface of from about 1.5 to about 5 g/m$^2$ and more typically from about 1 to about 3 g/m$^2$. When sulfuric acid is used for anodization, higher oxide weight (at least 3 g/m$^2$) can provide longer press life.

An interlayer can be formed by treatment of the aluminum support with, for example, a silicate, dextrine, calcium zirconium fluoride, hexafluorosilicic acid, poly(vinyl phosphonic acid) (PVPA), vinyl phosphonic acid copolymer, poly[(meth) acrylic acid], or acrylic acid copolymer to increase hydrophilicity. Still further, the aluminum support can be treated with a phosphate solution that can further contain an inorganic fluoride (PF). The aluminum support can be electrochemically-grained, sulfuric acid-anodized, and treated with PVPA or PF using known procedures to improve surface hydrophilicity.

The thickness of the substrate can be varied but should be sufficient to sustain the wear from printing and thin enough to wrap around a printing form. Useful embodiments include a treated aluminum foil having a thickness of at least 100 μm and up to and including 700 μm.

The backside (non-imaging side) of the substrate can be coated with antistatic agents and/or slipping layers or a matte layer to improve handling and "feel" of the lithographic printing plate precursor.

The substrate can also be a cylindrical surface having the imageable layer thereon, and thus be an integral part of the printing press. The use of such imaging cylinders is described for example in U.S. Pat. No. 5,713,287 (Gelbart).

A radiation-sensitive composition containing the components described above can be applied to the substrate as a solution or dispersion in a coating liquid using any suitable equipment and procedure, such as spin coating, knife coating, gravure coating, die coating, slot coating, bar coating, wire rod coating, roller coating, or extrusion hopper coating. The composition can also be applied by spraying onto a suitable support (such as an on-press printing cylinder).

Illustrative of such manufacturing methods is mixing the free radically polymerizable component, polymeric binder(s), initiator composition, radiation absorbing compound (or sensitizer), and any other components in a suitable coating solvent including water, organic solvents [such as glycol ethers including 1-methoxypropan-2-ol, methyl ethyl ketone (2-butanone), methanol, ethanol, 1-methoxy-2-propanol, iso-propyl alcohol, acetone, γ-butyrolactone, n-propanol, tetrahydrofuran, and others readily known in the art, as well as mixtures thereof], or mixtures thereof, applying the resulting solution to a substrate, and removing the solvent(s) by evaporation under suitable drying conditions. Some representative coating solvents and imageable layer formulations are described in the Examples below. After proper drying, the coating weight of the imageable layer is generally at least 0.1 and up to and including 5 g/m$^2$ or at least 0.5 and up to and including 3.5 g/m$^2$. Any particulate primary polymeric binders present in the imageable layer can partially coalesce or be deformed during the drying operation.

Layers can also be present under the imageable layer to enhance developability or to act as a thermal insulating layer. The underlying layer should be soluble or at least dispersible in the developer and typically have a relatively low thermal conductivity coefficient.

The lithographic printing precursor optionally includes what is conventionally known as an overcoat (also known as an "oxygen impermeable topcoat" or "oxygen barrier layer") disposed over the imageable layer. Such overcoat layers can comprise one or more poly(vinyl alcohol)s as the predominant polymeric binders, each of which has a hydrolysis level of up to 85%, typically from about 60 and up to and including 85% and more typically from about 75 and up to and including 85%. By "hydrolysis level", we are referring to the specific percentage of acetate moieties in the polymer having been converted to hydroxyl groups. Thus, vinyl acetate is polymerized to form poly(vinyl acetate) and a hydroxide (usually sodium or potassium hydroxide) is used to convert acetate groups to hydroxyl groups.

While the poly(vinyl alcohol)s described above can comprise up to 100% of the total overcoat dry weight, usually, they comprise at least 60 and up to 95% of the total overcoat dry weight. The overcoat thus can include up to 40 weight % of other components including but not limited to, other polymeric binders such as poly(vinyl pyrrolidone), poly(ethyleneimine), poly(vinyl imidazole), copolymers from two or more of vinyl pyrrolidone, ethyleneimine and vinyl imidazole, and mixtures of such polymers, and well as cationic, anionic, and non-ionic wetting agents or surfactants, flow improvers or thickeners, antifoamants, colorants, particles such as aluminum oxide and silicon dioxide, and biocides. Details about such addenda are provided in WO 99/06890 (Pappas et al.).

The overcoat coating weight is generally at least 0.1 and up to and including 4 g/m$^2$ and typically from about 1 to about 2.5 g/m$^2$.

The overcoat can be disposed over the imageable layer by applying a coating formulation containing the desired poly (vinyl alcohol) and any other components in a suitable solvent or mixture of solvents (such as isopropyl alcohol, water, or both) to the dried imageable layer, and suitable drying procedures.

Other topcoat layer polymer binders are also described in U.S. Pat. No. 3,458,311 (Alles), U.S. Pat. No. 4,072,527 (Fanni), and U.S. Pat. No. 4,072,528 (Bratt), and EP Publications 275,147A2 (Wade et al.), 403,096A2 (Ali), 354,475A2 (Zertani et al.), 465,034A2 (Ueda et al.), 352, 630A2 (Zertani et al.), 1,788,429 (Loccufier et al.), 1,788,431 (Van Damme et al.) and 1,788,434 (Van Damme et al.) and US Patent Application Publication 2005/0266349 (Van Damme et al.).

Intermediate drying steps can be used between applications of the various layer formulations to remove solvent(s) before coating other formulations. Drying steps at conventional times and temperatures can also help in preventing the mixing of the various layers.

Once the various layers have been applied and dried on the substrate, the lithographic printing precursor can be enclosed in water-impermeable material that substantially inhibits the transfer of moisture to and from the precursor as described in U.S. Pat. No. 7,175,969 (Ray et al.) that is incorporated herein by reference.

Positive-Working Lithographic Printing Precursors

Positive-working lithographic printing precursors can be single- or multi-layer imageable elements that generally rely on a radiation absorbing compound dispersed within one or more polymeric binders that, upon suitable irradiation, are soluble, dispersible, or removable in processing solutions including alkaline developers. Thus, the imageable layer, upon irradiation, undergoes a change in solubility properties with respect to the processing solution in its irradiated (exposed) regions.

For example, "single-layer" positive-working lithographic printing precursors are described for example, in WO 2004/081662 (Memetea et al.), U.S. Pat. No. 6,255,033 (Levanon et al.), U.S. Pat. No. 6,280,899 (Hoare et al.), U.S. Pat. No. 6,485,890 (Hoare et al.), U.S. Pat. No. 6,558,869 (Hearson et al.), U.S. Pat. No. 6,706,466 (Parsons et al.), U.S. Pat. No. 6,541,181 (Levanon et al.), U.S. Pat. No. 7,223,506 (Kitson et al.), U.S. Pat. No. 7,247,418 (Saraiya et al.), U.S. Pat. No. 7,270,930 (Hauck et al.), U.S. Pat. No. 7,279,263 (Goodin), and U.S. Pat. No. 7,399,576 (Levanon), EP 1,627,732 (Hatanaka et al.), and U.S. Published Patent Applications 2005/0214677 (Nagashima), 2004/0013965 (Memetea et al.), 2005/0003296 (Memetea et al.), and 2005/0214678 (Nagashima).

In general, single-layer lithographic printing precursors are formed by suitable application of an imageable layer formulation containing one or more polymeric binders and the discrete particles to a suitable substrate (described above) to form an imageable layer. The substrate can be treated to provide an "interlayer" for improved adhesion or hydrophilicity, and the single imageable layer is applied over the interlayer.

The single-layer, positive-working lithographic printing precursor also includes one or more radiation absorbing compounds (described above). While these compounds can be sensitive to any suitable energy form (including UV or visible radiation), they are usually sensitive to near-infrared or infrared radiation and thus, the radiation absorbing compounds having spectral sensitivity to from about 700 to about 1400 nm and typically from about 700 to about 1200 nm. Examples of suitable infrared radiation-sensitive compounds, including IR dyes are described above in relation to the negative-working lithographic printing precursors.

The radiation absorbing compound is generally present in the lithographic printing precursor in an amount sufficient to render the imageable layer insoluble to an aqueous developer after exposure to appropriate radiation. This amount is generally at least 0.5% and up to 30 weight % and typically from about 3 to about 10 weight % (based on total dry layer weight). In most embodiments, the radiation absorbing compound is present in the single imageable layer. Alternatively or additionally, radiation absorbing compounds may be located in a separate layer that is in thermal contact with the single imageable layer. Thus, during imaging, the action of the radiation absorbing compound can be transferred to the single imageable layer without the compound originally being incorporated into it.

In addition, solubility-suppressing components are optionally incorporated into the single imageable layer. Such components act as dissolution inhibitors that function as solubility-suppressing components for the polymeric binders. Dissolution inhibitors typically have polar functional groups that are believed to act as acceptor sites for hydrogen bonding with various groups in the polymeric binders. Useful dissolution inhibitors include triarylmethane dyes such as ethyl violet, crystal violet, malachite green, brilliant green, Victoria blue B, Victoria blue R, and Victoria pure blue BO, BASO-NYL® Violet 610 and D11 (PCAS, Longjumeau, France) but they are present in quantities insufficient to provide coloration as required for the present invention.

The polymeric binders used in the imageable layer are generally soluble in alkaline developers (defined below) after thermal imaging. The polymer(s) are present in an amount of at least 10 weight % and typically from about 20 to about 80 weight % of the total dry imageable layer weight.

Useful polymeric binders can be poly(vinyl phenols) or derivatives thereof, or phenolic polymers. They may include carboxylic (carboxy), sulfonic (sulfo), phosphonic (phosphono), or phosphoric acid groups that are incorporated into the polymer molecule. Other useful additional polymers include but are not limited to, novolak resins, resole resins, poly(vinyl acetals) having pendant phenolic groups, and mixtures of any of these resins (such as mixtures of one or more novolak resins and one or more resole resins). Typical novolak resins include but are not limited to, phenol-formaldehyde resins, cresol-formaldehyde resins, phenol-cresol-formaldehyde resins, p-t-butylphenol-formaldehyde resins, and pyrogallol-acetone resins, such as novolak resins prepared from reacting m-cresol or a m,p-cresol mixture with formaldehyde using conventional conditions. For example, some useful novolak resins include but are not limited to, xylenol-cresol resins, for example, SPN400, SPN420, SPN460, and VPN1100 (that are available from AZ Electronics) and EP25D40G and EP25D50G (noted below for the Examples) that have higher molecular weights, such as at least 4,000.

Other useful resins include polyvinyl compounds having phenolic hydroxyl groups, include poly(hydroxystyrenes) and copolymers containing recurring units of a hydroxystyrene and polymers and copolymers containing recurring units of substituted hydroxystyrenes. Also useful are branched poly(hydroxystyrenes) having multiple branched hydroxystyrene recurring units derived from 4-hydroxystyrene as described for example in U.S. Pat. No. 5,554,719 (Sounik) and U.S. Pat. No. 6,551,738 (Ohsawa et al.), and U.S. Published Patent Applications 2003/0050191 (Bhatt et al.), 2005/0051053 (Wisnudel et al.), and 2008/0008956 (Levanon et al.). For example, such branched hydroxystyrene polymers comprise recurring units derived from a hydroxystyrene, such as from 4-hydroxystyrene, which recurring units are further substituted with repeating hydroxystyrene units (such as 4-hydroxystyrene units) positioned ortho to the hydroxy group.

One group of useful polymeric binders are poly(vinyl phenol) and derivatives thereof. Such polymers are obtained generally by polymerization of vinyl phenol monomers, that is, substituted or unsubstituted vinyl phenols. Substituted vinyl phenol recurring units include those described below for the "a" recurring units in Structure (I). Some vinyl phenol copolymers are described in EP 1,669,803A (Barclay et al.).

Thermally imageable, multi-layer lithographic printing precursors are described, for example, in U.S. Pat. No. 6,294,311 (Shimazu et al.), U.S. Pat. No. 6,352,812 (Shimazu et al.), U.S. Pat. No. 6,593,055 (Shimazu et al.), U.S. Pat. No. 6,352,811 (Patel et al.), U.S. Pat. No. 6,358,669 (Savariar-Hauck et al.), U.S. Pat. No. 6,528,228 (Savariar-Hauck et al.), U.S. Pat. No. 7,163,770 (Saraiya et al.), U.S. Pat. No. 7,163,777 (Ray et al.), U.S. Pat. No. 7,186,482 (Kitson et al.), U.S. Pat. No. 7,223,506 (noted above), U.S. Pat. No. 7,229,744 (Patel), U.S. Pat. No. 7,241,556 (Saraiya et al.), U.S. Pat. No. 7,247,418 (noted above), U.S. Pat. No. 7,291,440 (Ray et al.), U.S. Pat. No. 7,300,726 (Patel et al.), and U.S. Pat. No. 7,338,745

(Ray et al.), and U.S. Patent Application Publications 2004/0067432 A1 (Kitson et al.) and 2005/0037280 (Loccufier et al.).

The inner layer is disposed between the outer layer and the substrate. Typically, it is disposed directly on the substrate. The inner layer comprises a predominant first polymeric material that is removable by the processing composition and preferably soluble in that solution to reduce sludging. In addition, this first polymeric material is preferably insoluble in the solvent used to coat the outer layer so that the outer layer can be coated over the inner layer without dissolving the inner layer. Mixtures of these first polymeric binders can be used if desired in the inner layer.

In some embodiments, the inner layer (and typically only the inner layer) further comprises an infrared radiation absorbing compound ("IR absorbing compounds") as described above that absorbs radiation from about at 600 nm to about 1500 and typically from about at 700 nm to about 1400 nm, with minimal absorption at from about 300 to about 600 nm. The infrared radiation absorbing compound can be present in the imageable element in an amount of generally from about 5% to about 30% and typically from about 12 to about 25%, based on the total dry weight of the element. This amount is based on the total dry weight of the layer in which it is located.

The ink-receptive outer layer of the lithographic printing precursor is disposed over the inner layer and in typical embodiments there are no intermediate layers between the inner and outer layers. The outer layer comprises a polymeric material that is different than the first polymeric binder described above. The outer layer is substantially free of infrared radiation absorbing compounds, meaning that none of these compounds are purposely incorporated therein and insubstantial amounts diffuse into it from other layers.

Thus, the outer layer comprises a polymeric binder that is a light-stable, water-insoluble, alkaline developer soluble, film-forming binder material such as phenolic resins, urethane resins, and polyacrylates. Particularly useful binder materials are described, for example in U.S. Pat. No. 6,352,812 (noted above), U.S. Pat. No. 6,358,669 (noted above), U.S. Pat. No. 6,352,811 (noted above), U.S. Pat. No. 6,294,311 (noted above), U.S. Pat. No. 6,893,783 (Kitson et al.), and U.S. Pat. No. 6,645,689 (Jarek), U.S. Patent Application Publications 2003/0108817 (Patel et al) and 2003/0162126 (Kitson et al.), and WO 2005/018934 (Kitson et al.).

Other useful film-forming polymeric binders for the outer layer are phenolic resins or hydroxy-containing polymers containing phenolic monomeric units that can be random, alternating, block, or graft copolymers of different monomers and may be selected from polymers of vinyl phenol, novolak resins, or resole resins.

Useful poly(vinyl phenol) resins can be polymers of one or more hydroxyphenyl containing monomers such as hydroxystyrenes and hydroxyphenyl(meth)acrylates. Other monomers not containing hydroxy groups can be copolymerized with the hydroxy-containing monomers. These resins can be prepared by polymerizing one or more of the monomers in the presence of a radical initiator or a cationic polymerization initiator using known reaction conditions.

Examples of useful hydroxy-containing polymers include ALNOVOL SPN452, SPN400, HPN100 (Clariant GmbH), DURITE PD443, SD423A, SD126A, PD494A, PD-140 (Hexion Specialty Chemicals, Columbus, Ohio), BAKELITE 6866LB02, AG, 6866LB03 (Bakelite AG), KR 400/8 (Koyo Chemicals Inc.), HRJ 1085 and 2606 (Schenectady International, Inc.), and Lyncur CMM (Siber Hegner), all of which are described in U.S. Patent Application Publication 2005/0037280 (noted above).

Useful novolak resins in the upper layer can be non-functionalized, or functionalized with polar groups including but not limited to, diazo groups, carboxylic acid esters (such as acetate benzoate), phosphate esters, sulfonate esters, sulfonate esters (such as methyl sulfonate, phenyl sulfonate, tosylate, 2-nitrobenzene tosylate, and p-bromophenyl sulfonate), and ethers (such as phenyl ethers). The phenolic hydroxyl groups can be converted to -T-Z groups in which "T" is a polar group and "Z" is another non-diazide functional group (as described for example in WO 99/01795 of McCullough et al. and U.S. Pat. No. 6,218,083 of McCullough et al.). The phenolic hydroxyl groups can also be derivatized with diazo groups containing o-naphthoquinone diazide moieties (as described for example in U.S. Pat. Nos. 5,705,308 and 5,705,322 both of West et al.).

Useful polymeric binders in the outer layer include copolymers comprising recurring units derived from styrene or a styrene derivative and recurring units derived from maleic anhydride, copolymers comprising recurring units derived from a (meth)acrylate and recurring units derived from a (meth)acrylic acid, or mixtures of both types of copolymers. Further details of these types of copolymers are described in U.S. Patent Application Publication 2007/0065737 (Kitson et al.).

In some embodiments, the outer layer may further include a monomeric or polymeric compound that includes a benzoquinone diazide and/or naphthoquinone diazide moiety. The polymeric compounds can be phenolic resins derivatized with a benzoquinone diazide or naphthoquinone diazide moiety as described for example in U.S. Pat. No. 5,705,308 (West et al.) and U.S. Pat. No. 5,705,322 (West et al.). Mixtures of such compounds can also be used. An example of a useful polymeric compound of this type is P-3000, a naphthoquinone diazide of a pyrogallol/acetone resin (available from PCAS, France). Other useful compounds containing diazide moieties are described for example in U.S. Pat. No. 6,294,311 (noted above) and U.S. Pat. No. 5,143,816 (Mizutani et al.).

Coalesceable Lithographic Printing Precursors

Some lithographic printing precursors useful in this invention have a single thermally-sensitive imageable layer containing an infrared radiation absorbing compound and core-shell particles that coalesce upon thermal imaging. This imageable layer is disposed on a suitable substrate. The core of the core-shell particles is composed of a hydrophobic thermoplastic polymer and the shell of the core-shell particles is composed of a hydrophilic polymer that is covalently bonded to the core hydrophobic thermoplastic polymer.

Other lithographic printing plate precursors having coalesceable imageable layers are described in many publications including but not limited to, U.S. Pat. No. 6,218,073 (Shimizu et al.), U.S. Pat. No. 6,509,133 (Watanabe et al.), U.S. Pat. No. 6,627,380 (Saito et al.), U.S. Pat. No. 6,692,890 (Huang et al.), U.S. Pat. No. 6,030,750 (Vermeersch et al.), U.S. Pat. No. 6,110,644 (Vermeersch et al.), U.S. Pat. No. 5,609,980 (Matthews et al.), and EP 514,145 A1 (Matthews et al.) and EP 1,642,714 A1 (Wilkinson et al.), all of which are incorporated herein by reference. Still other precursors and methods of providing an image are described in copending and commonly assigned U.S. Patent Application Publication 2009/0183647 (Jarek) that is incorporated herein by reference.

Imaging Conditions

During use, the lithographic printing precursors are exposed to a suitable source of imaging or exposing radiation at a wavelength of from about 150 to about 1500 nm. For example, imaging can be carried out using imaging or exposing radiation, such as from an infrared laser at a wavelength of at least 700 nm and up to and including about 1400 nm and typically at least 750 nm and up to and including 1200 nm. Imaging can be carried out using imaging radiation at multiple wavelengths at the same time if desired. Other imageable elements, especially negative-working imageable elements can be exposed to a suitable source of UV, "violet", or visible imaging radiation.

Thus, in some embodiments of the method of this invention, the lithographic printing precursor can have a spectral sensitivity to imagewise exposure that is carried out at a wavelength of from about 150 to about 450 nm, or to imagewise exposure that is carried out at a wavelength of from about 700 to about 1400 nm.

The laser used to expose the lithographic printing precursor is usually a diode laser, because of the reliability and low maintenance of diode laser systems, but other lasers such as gas or solid-state lasers may also be used. The combination of power, intensity and exposure time for laser imaging would be readily apparent to one skilled in the art.

The imaging apparatus can function as a platesetter. The imaging apparatus can be configured as a flatbed recorder or as a drum recorder, with the imageable member mounted to the interior or exterior cylindrical surface of the drum. An example of an useful near-infrared and infrared imaging apparatus is available as models of Creo Trendsetter or Creo Quantum 800 imagesetters available from Eastman Kodak Company (Burnaby, British Columbia, Canada) that contain laser diodes that emit near infrared radiation at a wavelength of about 830 nm. Other suitable imaging sources include the Crescent 42T Platesetter that operates at a wavelength of 1064 nm (available from Gerber Scientific, Chicago, Ill.) and the Screen PlateRite 4300 series or 8600 series platesetter (available from Screen, Chicago, Ill.).

Imaging with infrared radiation can be carried out generally at imaging energies of at least 30 mJ/cm$^2$ and up to and including 500 mJ/cm$^2$, and typically at least 50 and up to and including 300 mJ/cm$^2$ depending upon the sensitivity of the imageable layer.

Useful UV and "violet" imaging apparatus include Prosetter (from Heidelberger Druckmaschinen, Germany), Luxel V-8 (from FUJI, Japan), Python (Highwater, UK), MakoNews, Mako 2, Mako 4 or Mako 8 (from ECRM, US), Micra (from Screen, Japan), Polaris and Advantage (from AGFA, Belgium), Laserjet (from Krause, Germany), and Andromeda® A750M (from Lithotech, Germany), imagesetters.

Imaging radiation in the UV to visible region of the spectrum, and particularly the UV region (for example at least 150 nm and up to and including 450 nm), can be carried out generally using energies of at least 0.01 mJ/cm$^2$ and up to and including 0.5 mJ/cm$^2$, and typically at least 0.02 and up to and including about 0.1 mJ/cm$^2$. It would be desirable, for example, to image the UV/visible radiation-sensitive imageable elements at a power density in the range of at least 0.5 and up to and including 50 kW/cm$^2$ and typically of at least 5 and up to and including 30 kW/cm$^2$.

After imaging of negative-working lithographic printing precursors, a heating step might be used to accelerate the formation of a latent image. This heating step can be realized in so called "preheat units" that can be a separate machine or integrated into the processor that develops the imaged element. There are different types of preheat units. The most common ones use infrared radiation or hot air circulation, or combination thereof, to heat the imaged element. The temperature used for the purpose is from about 70 to about 200° C. and typically from about 90 to about 160° C.

Before developing the imaged precursor, a pre-rinse step might be carried out especially for the negative-working lithographic printing precursors having a protective oxygen barrier or topcoat. This pre-rinse step can be carried out in a stand-alone apparatus or by manually rinsing the imaged precursor with water or the pre-rinse step can be carried out in a washing unit that is integrated in a processor used for developing the imaged precursor.

Development and Printing

With or without the need for a preheat step after imaging, the imaged lithographic printing precursors can be developed "off-press" using conventional processing and an aqueous processing solution such as an aqueous developer. For example, the imaged precursor can be processed in a developer prior to step B described (contact with the coloration solution).

As one skilled in the art would understand, the best developers (processing solutions) for negative-working lithographic printing precursors will likely be different than the best developers for the single- or multi-layer positive lithographic printing precursors. A skilled worker would be able to determine from the level of skill and teaching in the art which developers are best with a given type of lithographic printing precursor.

The processing solutions generally include surfactants, chelating agents (such as salts of ethylenediaminetetraacetic acid), organic solvents (such as benzyl alcohol), and alkaline components (such as inorganic metasilicates, organic metasilicates, hydroxides, and bicarbonates). The pH of such solutions is generally from about 4 to about 14 or more likely from about 4 to about 7.5. Aqueous alkaline developers and organic solvent-containing alkaline developers can be used. Acids or alkaline compounds that create a certain pH, as well as buffers that maintain the pH, can be added. Useful compounds of this type include but are not limited to, citric acid, acetic acid, and triethanolamine. Acidic processing solutions (described in detail below) are also useful.

The developer can also include one or more surfactants including nonionic surfactants, anionic surfactants, cationic surfactants, amphoteric surfactants, and fluorine-containing surfactants. Useful nonionic surfactants include one or more from one or more of the following classes of compounds: polyoxyethylene alkyl ethers, polyoxyethylene alkylphenylethers, polyoxyethylene polystyrylphenyl ethers, polyoxyethylene polyoxypropylene alkyl ethers, polyoxyethylene sorbitan fatty acid partial esters, polyoxyethylene sorbitol fatty acid partial esters, polyethylene glycol fatty acid esters, fatty acid diethanolamides, polyoxyethylene alkylamines, triethanolamine fatty acid esters, trialylamine oxides, and copolymers of polyethylene glycol and polypropylene glycol.

Useful anionic surfactants include but are not limited to, fatty acid salts, abietic acid salts, hydroxyalkanesulfonic acid salts, alkanesulfonic acid salts, dialkylsulfosuccinic ester salts, alkylbenzenesulfonic acid salts, alkylnaphthalenesulfonic acid salts, alkylphenoxypolyoxy ethylene propylsulfonic acid salts, polyoxyethylene alkylsulfophenyl ether salts, N-alkylsulfosuccinic acid monoamide disodium salts, alkyl/aryl sulfonic acid salts, and alkyl sulfate ester salts.

Organic solvent-containing alkaline developers are generally single-phase solutions of one or more organic solvents that are miscible with water, and generally have a pH of from 8 to 12. Useful organic solvents include the reaction products of phenol with ethylene oxide and propylene oxide [such as ethylene glycol phenyl ether (phenoxyethanol)], benzyl alcohol, esters of ethylene glycol and of propylene glycol with acids having 6 or less carbon atoms, and ethers of ethylene glycol, diethylene glycol, and of propylene glycol with alkyl groups having 6 or less carbon atoms, such as 2-ethylethanol, 2-butoxyethanolethylene glycol, diethylene glycol, di- and tri-ethanol amine, propanol and isopropanol, and cyclohexanol, diethylene glycol dimethyl ether. The organic solvent(s) is generally present in an amount of from about 0.5 to about 15% based on total developer weight.

Representative organic solvent-containing alkaline developers include ND-1 Developer, 955 Developer, 956 Developer, 989 Developer, Developer 980, and 956 Developer (available from Eastman Kodak Company), HDN-1 Developer and LP-DS Developer (available from Fuji Photo), and EN 232 Developer and PL10 Developer (available from Agfa).

Useful aqueous alkaline developers generally have a pH of at least 7 and typically from about 10 to about 14, or more typically from 11 to 13.5. Such developers include but are note limited to, 3000 Developer, 9000 Developer, Goldstar® Developer, Goldstar® Plus Developer, Goldstar® Premium Developer, GREENSTAR Developer, ThermalPro Developer, PROTHERM Developer, MX1813 Developer, and MX1710 Developer (all available from Eastman Kodak Company), as well as Fuji HDP7 Developer (Fuji Photo), and Energy CTP Developer (Agfa). These compositions also generally include surfactants, chelating agents (such as salts of ethylenediaminetetraacetic acid), and alkaline components (such as inorganic metasilicates, organic metasilicates, hydroxides, and bicarbonates).

Such alkaline developers can also include one or more "coating-attack suppressing agents" that are developer-soluble compounds that suppress developer attack of the outer layer. "Developer-soluble" means that enough of the agent(s) will dissolve in the developer to suppress attack by the developer. Mixtures of these compounds can be used. Typically, the coating-attack suppressing agents are developer-soluble polyethoxylated, polypropoxylated, or polybutoxylated compounds that include recurring —(CH$_2$—CHR$_a$—O—)— units in which R$_a$ is hydrogen or a methyl or ethyl group. Each agent can have the same or different recurring units (in a random or block fashion). Representative compounds of this type include but are not limited to, polyglycols and polycondensation products having the noted recurring units. Examples of such compounds and representative sources, tradenames, or methods of preparing are described for example in U.S. Pat. No. 6,649,324 (Fiebag et al.).

Processing solutions having a pH of from about 4 to about 11 are also useful for developing imaged lithographic printing precursors in the absence of post-rinse and gumming steps after development (so called "single bath development"). Such processing solutions contain in most cases hydrophilic polymers like gum Arabic, polyvinyl alcohol, poly(acrylic acid), or other hydrophilic polymers to protect the developed printing member against fingerprints and to prevent toning of the printing member when used on a printing press.

Generally, a processing solution is applied to the imaged precursor by rubbing or wiping the outer layer with an applicator containing the developer. Alternatively, the imaged precursor can be brushed with the processing solution or it may be applied by spraying the outer layer with sufficient force to remove the exposed regions. Still again, the imaged precursor can be immersed in the procession solution. These development processes can be carried out in suitable developing processors or equipment using standard residence times and recirculation and replenishment rates.

In alternative embodiments, with or without a post-exposure baking step after imaging and before development, the imaged precursors can be developed "off-press" using a gum processing solution or single bath developer as described below. A gum solution is typically an aqueous liquid that comprises one or more surface protective compounds capable of protecting the lithographic image of the printing plate against contamination (for example, oxidation, fingerprints, dust or scratches).

The gum may be provided in diluted or concentrated form. The amounts of components described below refer to amount in the diluted gum that is likely its form for use in the practice of the invention. However, it is to be understood that concentrated gums can be used and the amounts of various components (such as the anionic surfactants) would be correspondingly increased.

The gum is an aqueous solution that generally has a pH greater than 3 and up to about 9 as adjusted using a suitable amount of a base. The viscosity of the gum can be adjusted to a value of from about 1.7 to about 5 cP by adding a suitable amount of a viscosity increasing compound such as a poly(vinyl alcohol) or poly(ethylene oxide).

In addition, these gums have one or more anionic surfactants as the only essential component, even though optional components (described below) can be present if desired. Useful anionic surfactants include those with carboxylic acid, sulfonic acid, or phosphonic acid groups (or salts thereof). Anionic surfactants having sulfonic acid (or salts thereof) groups are particularly useful. Particular examples of such surfactants include but are not limited to, sodium dodecylphenoxyoxybenzene disulfonate, the sodium salt of alkylated naphthalenesulfonate, disodium methylene-dinaphthalene disulfonate, sodium dodecylbenzenesulfonate, sulfonated alkyl-diphenyloxide, ammonium or potassium perfluoroalkylsulfonate and sodium dioctylsulfosuccinate.

The gums may include nonionic surfactants as described in [0029] or hydrophilic polymers described in [0024] of EP 1,751,625 (noted above), incorporated herein by reference. Particularly useful nonionic surfactants include Mazol® PG031-K (a triglycerol monooleate, Tween® 80 (a sorbitan derivative), Pluronic® L62LF (a block copolymer of propylene oxide and ethylene oxide), and Zonyl® FSN (a fluorocarbon), and a nonionic surfactant for successfully coating the gum onto the printing member surface, such as a nonionic polyglycol. These nonionic surfactants can be present in an amount of up to 10 weight %, but at usually less than 2 weight %.

Other optional components of the gum include inorganic salts (such as those described in [0032] of U.S. Patent Application 2005/0266349, noted above), wetting agents (such as a glycol), a metal chelating agents, antiseptic agents, anti-foaming agents, ink receptivity agents (such as those described in [0038] of U.S. Pat. No. '349), and viscosity increasing agents as noted above. The amounts of such components are known in the art. Calcium ion chelating agents are particularly useful, including but not limited to, polyaminopoly-carboxylic acids, aminopolycarboxylic acids, or salts thereof, [such as salts of ethylenediaminetetraacetic acid (EDTA, sodium salt)], organic phosphonic acids and salts thereof, and phosphonoalkanetricarboxylic acids and salts thereof. Organic amines may also be useful. A chelating agent may be present in the gum in an amount of from about 0.001 to about 1 weight %.

Generally, the gum is applied to the imaged precursor by rubbing, spraying, jetting, dipping, coating, or wiping the outer layer with the gum or a roller, impregnated pad, or applicator containing the gum. For example, the imaged precursor can be brushed with the gum, or the gum may be poured on or applied by spraying the outer layer with sufficient force to remove the exposed regions using a spray nozzle system as described for example in [0124] of EP 1,788,431A2 (noted above). Still again, the imaged precursor can be immersed in the gum and rubbed by hand or with an apparatus.

The gum can also be applied in a gumming unit (or gumming station) that has at least one roller for rubbing or brushing the lithographic printing member while the gum is applied during development. By using such a gumming unit, the non-exposed regions of the imaged layer may be removed from the substrate more completely and quickly. The gum used in development can be collected in a tank and the gum can be used several times, and replenished if necessary from a reservoir of gum. The gum replenisher can be of the same concentration as that used in development, or be provided in concentrated form and diluted with water at an appropriate time.

Following off-press development, a postbake operation can be carried out, with or without a blanket or floodwise exposure to UV or visible radiation. The lithographic printing member can be baked in a postbake operation to increase its run length. Baking can be carried out, for example at from about 170° C. to about 240° C. for from about 7 to about 10 minutes, or at about 120° C. for 30 minutes. Alternatively, a blanket UV or visible radiation exposure can be carried out, without a postbake operation. In addition, before any postbake operation, the lithographic printing member can be rinsed with water or an aqueous solution.

Thus, whatever the developing process, the method of this invention can be carried out by omitting the post-exposure baking step and removing predominantly only the non-exposed regions by development to provide a negative-working lithographic printing member having a hydrophilic aluminum-containing substrate.

Alternatively, predominantly only the exposed regions are removed during developing to provide a positive-working lithographic printing member having a hydrophilic aluminum-containing substrate.

As one skilled in the art would know, such development processes may remove insignificant amounts of the exposed regions (for negative-working) or non-exposed regions (for positive-working), but not enough to significantly affect the desired image.

Printing can be carried out by applying a lithographic ink and fountain solution to the printing surface of the lithographic printing member. The fountain solution is taken up by the non-imaged regions, that is, the surface of the hydrophilic substrate revealed by the imaging and development steps, and the ink is taken up by the imaged (non-removed) regions of the imaged layer. The ink is then transferred to a suitable receiving material (such as cloth, paper, metal, glass, or plastic) to provide a desired impression of the image thereon. Typically, an intermediate "blanket" roller can be used to transfer the ink from the imaged member to the receiving material. The lithographic printing members can be cleaned between impressions, if desired, using conventional cleaning means.

Use of Photochromic Compounds

The photochromic compounds (colorless form), such as those described above in Structure (I), can be added to an acidic or alkaline developer (processing solution) as the coloration solution for Step B to avoid using an extra "coloration" step. When used in this manner, one or more photochromic compounds are present in an amount of at least 0.005 weight % and up to and including 2 weight %. More typically, the amount of the photochromic compounds is from about 0.01 to about 0.5 weight %.

As noted above, it may be useful to dissolve or disperse the photochromic compound(s), such as those described above in Structure (I), in an organic solvent or mixture of organic solvents before it is added to the acidic or alkaline coloration solution, or to a developer. Useful organic solvents include but are not limited to, butoxyethanol, γ-butyrolactone, diethanol amine, benzyl alcohol, phenoxyethanol, ethylene glycol monomethyl ether, propylene glycol monomethyl ether, propylene glycol methyl ether acetate, dipropylene (or ethylene) glycol monomethyl ether, toluene, kerosene, mineral spirits, dichloroethane, diethylene glycol dimethyl ether and tetrachloroethane. Benzyl alcohol, phenoxy ethanol, γ-butyrolactone, diacetone alcohol glycol ester, an alkyl lactate, toluene, diethylene glycol dimethyl ether, or a combination of any of these, is particularly useful. For example, the organic solvents are present in an amount of from about 1 to about 25 weight %.

After development, the imaged lithographic printing member is exposed to suitable UV radiation to change the photochromic compound to its colored form. The conditions for this color formation would be readily apparent to a skilled worker and can vary in time, temperature, and imaging strength. For example, UV exposure can be carried out at a $\lambda_{max}$ of from about 350 nm to about 380 nm at 120 watts over an exposure width of 80 cm and a dwell time of from about 20 to about 90 seconds. The lithographic printing member can be optionally dried before UV exposure although wet UV exposure is also useful.

Alternatively, the photochromic compound can be applied (in Step B) to the lithographic printing member in a separate aqueous coloration solution that can be applied by hand or in a separate stage after development but before UV exposure (Step C). The lithographic printing member can be dried prior to application of the coloration solution or not. In addition, it can be dried after application of the coloration solution (Step B) and before UV radiation exposure (Step C) or the UV exposure (Step C) can be carried out before drying. By "coloration solution", we intend to include dispersions or suspensions of the photochromic compounds.

The photochromic compound(s) can also be added to the gum solutions described above, some of which are conventionally used after development in the preparation of lithographic printing plates. Alternatively, the photochromic compound(s) can be used in the gum solutions described above that are used for "processing" or development.

The photochromic compound(s) described above, such as those defined by Structure (I), is present in the coloration solution in an amount of at least 0.005 weight % and up to and including 2 weight %, or typically from about 0.01 to about 0.5 weight %. As noted above, they can be incorporated into the coloration solution in the form of a solution or dispersion in one or more organic solvents. Generally, the amount of organic solvents in the coloration solution is from about 1 to about 25 weight %. The coloration solution can also include one or more surfactants as described above for the developers. The pH of the acidic coloration solution can be generally from about 4 to about 7.5 and can be adjusted using suitable acids or bases. For example, the coloration solution can be an acidic processing solution that is capable of developing the imaged precursor.

Whether the photochromic compound is used within a developer or a separate coloration solution, it is also possible to add it to the desired solution while that solution is being circulated within the processing machine. For example, the photochromic compound can be added to the coloration solution after development as the coloration solution is being circulated within the processing machine. Alternatively, the photochromic compound can be added to the developer or coloration solution just before its use in Step B.

After the coloration solution has been applied and the lithographic printing member has been exposed to UV radiation (and dried if necessary), the lithographic printing member can be used for lithographic printing as described above.

The present invention provides at least the following embodiments and combinations thereof, but other combinations of features are considered to be within the present invention as a skilled artisan would appreciate from the teaching of this disclosure:

1. A method of providing a lithographic printing member comprising:
    A) imagewise exposing a lithographic printing precursor comprising a substrate and an imageable layer to provide an imaged precursor having exposed and non-exposed regions in the imageable layer,
    B) contacting the imaged precursor with a coloration solution containing a photochromic compound, and
    C) exposing the imaged precursor after step B to ultraviolet (UV) light to effect color change of the photochromic compound attached to the imageable layer.

2. The method of embodiment 1 wherein the photochromic compound is a dithienethylene having one or more attached electron donating groups.

3. The method of embodiment 1 or 2 wherein the photochromic compound is stable at room temperature when exposed to 500 lumens of visible light for 100 hours.

4. The method of any of embodiments 1 to 3 wherein the photochromic compound is represented by the following Structure (I):

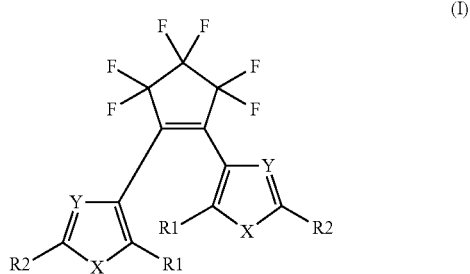

wherein X is oxygen, sulfur, sulfone, or a substituted or unsubstituted nitrogen, Y is oxygen or a substituted or unsubstituted carbon, $R^1$ is an electron donating group, and $R^2$ is hydrogen or any other substituent.

5. The method of embodiment 4 wherein $R^1$ is an alkoxy group having at least 2 carbon atoms, cycloalkoxy group having at least 5 carbon atoms in the carbocyclic ring, aryloxy group having at least 6 carbon atoms in the carbocyclic ring, —S—$R^3$ wherein $R^3$ is a substituted or unsubstituted alkyl group having 1 to 6 carbon atoms, substituted or unsubstituted cycloalkyl group having 5 to 8 carbon atoms in the hydrocarbon ring, substituted or unsubstituted aryl group having 6 or 10 carbon atoms in the aromatic carbocyclic ring, or —Z'($R^4$)($R^5$) wherein Z' is a nitrogen atom, and $R^4$ and $R^5$ are the same or different substituted or unsubstituted alkyl groups having 1 to 5 carbon atoms, or substituted or unsubstituted aryl groups such as substituted or unsubstituted phenyl or naphthyl groups, and $R^2$ is hydrogen or an alkyl, aryl, cycloalkyl, alkoxy, cycloalkoxy, dialkylamino, or aryl group, or $R^2$ can be joined with the Y group on the same ring to form a fused ring system.

6. The method of embodiment 4 or 5 wherein $R^1$ an alkoxy group having at least 2 carbon atoms, cycloalkoxy group having at least 5 carbon atoms in the carbocyclic ring, or aryloxy group having at least 6 carbon atoms in the carbocyclic ring.

7. The method of any of embodiments 1 to 6 wherein the imaged precursor is processed in a developer prior to step B.

8. The method of any of embodiments 1 to 7 wherein the coloration solution used in step B is an acidic processing solution capable of developing the imaged precursor.

9. The method of any of embodiments 1 to 7 wherein the coloration solution used in step B is an alkaline processing solution capable of developing the imaged precursor.

10. The method of any of embodiments 1 to 9 wherein the imaged precursor is dried between steps B and C.

11. The method of any of embodiments 1 to 9 wherein the imaged precursor is dried after step C.

12. The method of any of embodiments 1 to 11 wherein the photochromic compound is added to the coloration solution just before its use in step B.

13. The method of embodiment 12 that is carried out in a processing machine wherein the photochromic compound is added to the coloration solution as the coloration solution is being circulated within the processing machine.

14. The method of any of embodiments 1 to 13 wherein the photochromic compound is present in the coloration solution in an amount of at least 0.005 weight % and up to and including 2 weight %.

15. The method of any of embodiments 1 to 14 wherein the coloration solution has a pH of from about 4 to about 7.5.

16. The method of any of embodiments 1 to 15 wherein the coloration solution comprises one or more organic solvents in an amount of from about 1 to about 25 weight %, the organic solvents being present to dissolve or disperse the photochromic compound.

17. The method of any of embodiments 1 to 16 wherein the UV exposure is carried out using UV radiation having a $\lambda_{max}$ of from about 350 nm to about 390 nm at 120 watts over a exposure width of 80 cm and a dwell time of from about 20 to about 90 seconds.

18. The method of any of embodiments 1 to 17 wherein the lithographic printing plate precursor is a negative-working lithographic printing plate precursor and the imageable layer is a negative-working imageable layer that comprises a free radically polymerizable component, a free radical initiator composition, a radiation absorbing compound, and a polymeric binder.

19. The method of any of embodiments 1 to 18 wherein the lithographic printing plate precursor is imagewise exposed either at a wavelength of from about 700 nm to about 1400 nm or at a wavelength of from about 150 nm to about 450 nm.

20. The method of embodiment 18 or 19 wherein the lithographic printing plate precursor further comprises a water-soluble topcoat disposed on the negative-working imageable layer.

21. An alkaline coloration solution having a pH of from about 10 to about 14, and comprising a photochromic compound that is represented by the following Structure (I):

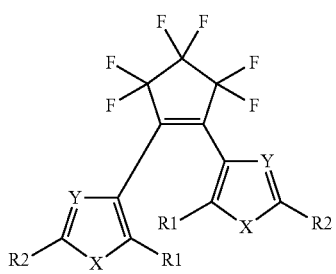

(I)

wherein X is oxygen, sulfur, sulfone, or a substituted or unsubstituted nitrogen, Y is oxygen or a substituted or unsubstituted carbon, $R^1$ is an electron donating group, and $R^2$ is hydrogen or any other substituent.

22. The alkaline coloration solution of embodiment 21 wherein $R^1$ is an alkoxy group having at least 2 carbon atoms, cycloalkoxy group having at least 5 carbon atoms in the carbocyclic ring, aryloxy group having at least 6 carbon atoms in the carbocyclic ring, —S—$R^3$ wherein $R^3$ is a substituted or unsubstituted alkyl group having 1 to 6 carbon atoms, substituted or unsubstituted cycloalkyl group having 5 to 8 carbon atoms in the hydrocarbon ring, substituted or unsubstituted aryl group having 6 or 10 carbon atoms in the aromatic carbocyclic ring, or —Z'($R^4$)($R^5$) wherein Z' is a nitrogen atom, and $R^4$ and $R^5$ are the same or different substituted or unsubstituted alkyl groups having 1 to 5 carbon atoms, or substituted or unsubstituted aryl groups such as substituted or unsubstituted phenyl or naphthyl groups, and $R^2$ is hydrogen or an alkyl, aryl, cycloalkyl, alkoxy, cycloalkoxy, dialkylamino, or aryl group, or $R^2$ can be joined with the Y group on the same ring to form a fused ring system.

23. The alkaline coloration solution of embodiment 21 or 22 wherein $R^1$ is an alkoxy group having at least 2 carbon atoms, cycloalkoxy group having at least 5 carbon atoms in the carbocyclic ring, or aryloxy group having at least 6 carbon atoms in the carbocyclic ring.

24. The alkaline coloration solution of any of embodiments 21 to 23 that further comprises from about 1 to about 25 weight % of an organic solvent that dissolves or disperses the photochromic compound, which organic solvent includes one or more of benzyl alcohol, phenoxy ethanol, γ-butyrolactone, diacetone alcohol glycol ester, an alkyl lactate, toluene, and diethylene glycol dimethyl ether.

25. An acidic coloration solution having a pH of from about 4 to about 7.5 and comprising a photochromic compound that is represented by the following Structure (I):

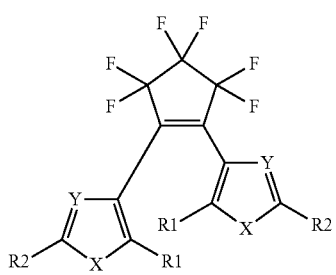

(I)

wherein X is oxygen, sulfur, sulfone, or a substituted or unsubstituted nitrogen, Y is oxygen or a substituted or unsubstituted carbon, $R^1$ is an electron donating group, and $R^2$ is hydrogen or any other substituent.

26. The acidic coloration solution of embodiment 25 wherein $R^1$ is an alkoxy group having at least 2 carbon atoms, cycloalkoxy group having at least 5 carbon atoms in the carbocyclic ring, aryloxy group having at least 6 carbon atoms in the carbocyclic ring, —S—$R^3$ wherein $R^3$ is a substituted or unsubstituted alkyl group having 1 to 6 carbon atoms, substituted or unsubstituted cycloalkyl group having 5 to 8 carbon atoms in the hydrocarbon ring, substituted or unsubstituted aryl group having 6 or 10 carbon atoms in the aromatic carbocyclic ring, or —Z'($R^4$)($R^5$) wherein Z' is a nitrogen atom, and $R^4$ and $R^5$ are the same or different substituted or unsubstituted alkyl groups having 1 to 5 carbon atoms, or substituted or unsubstituted aryl groups such as substituted or unsubstituted phenyl or naphthyl groups, and $R^2$ is hydrogen or an alkyl, aryl, cycloalkyl, alkoxy, cycloalkoxy, dialkylamino, or aryl group, or $R^2$ can be joined with the Y group on the same ring to form a fused ring system.

27. The acidic coloration solution of embodiment 25 or 26 wherein $R^1$ is an alkoxy group having at least 2 carbon atoms, cycloalkoxy group having at least 5 carbon atoms in the carbocyclic ring, or aryloxy group having at least 6 carbon atoms in the carbocyclic ring.

28. The acidic coloration solution of any of embodiments 25 to 27 that further comprises from about 1 to about 25 weight % of an organic solvent that dissolves or disperses the photochromic compound, which organic solvent includes one or more of benzyl alcohol, phenoxy ethanol, γ-butyrolactone, diacetone alcohol glycol ester, an alkyl lactate, toluene, and diethylene glycol dimethyl ether.

The following Examples are used to illustrate the practice of this invention and are not meant to be limiting in any manner.

A colorless form of representative photochromic compounds that are useful in the practice of this invention was prepared in the following manner:

Synthesis:

The synthesis of dithienylethene derivatives with various types of substituents is illustrated, for example, by the following synthetic scheme with 1,2-bis(2-cyclohexyloxy-5-phenyl-3-thienyl)perfluorocyclopentene:

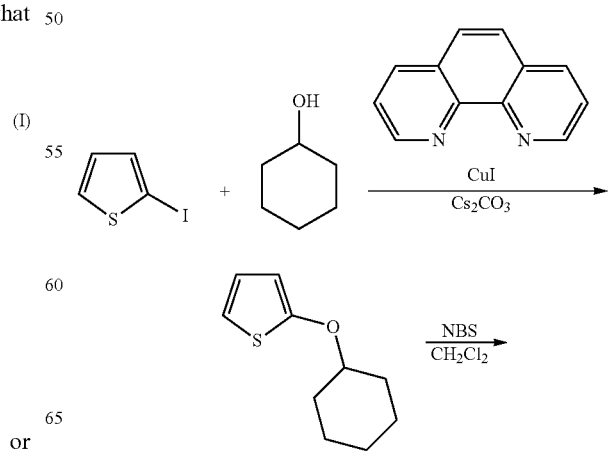

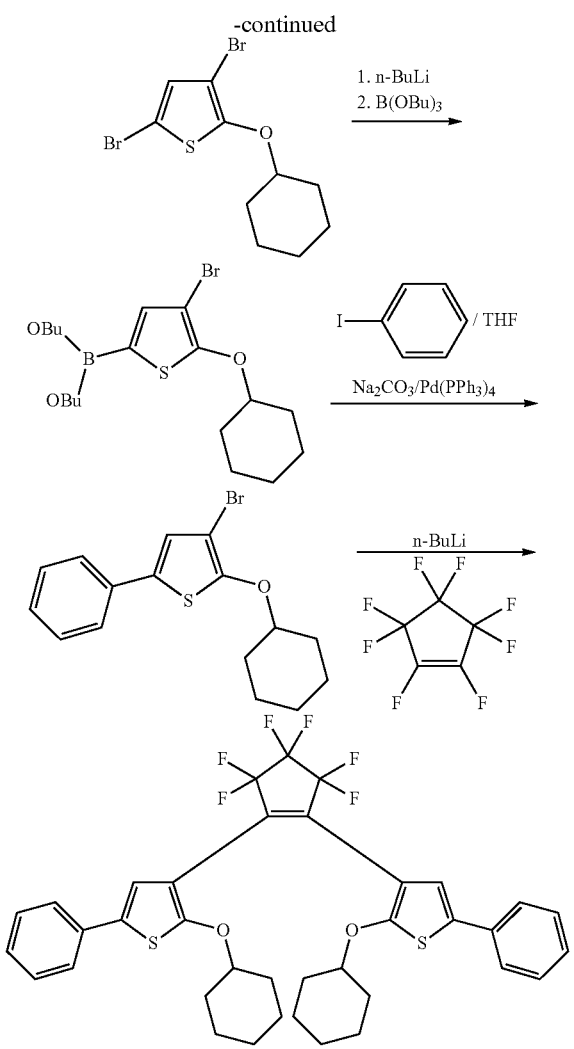

A sealed bottle containing 2-iodothiophene (28 g, 0.13 mol), cyclohexanol (140 ml) in the presence of catalytic cuprous iodide (2.7 g, 13.5 mmol), 1,10-phenanthroline (5 g, 27.7 mmol), and cesium carbonate (86 g, 0.26 mol) was heated at 110° C. for 24 hours. The mixture was then cooled to room temperature and filtered though a pad of silica gel eluted with heptanes. The filtrate was concentrated and purified through a silica gel column using heptanes as eluent to give 2-cyclohexythiophene (15 g, 70% yield).

To a solution of 2-cyclohexythiophene (15 g, 82.8 mmol) dissolved in dichloromethane (180 ml) at 0° C. was slowly added NBS (29 g, 166 mmol). The resulting mixture was then stirred at room temperature overnight. The mixture was then cooled at 0° C. and the solid was filtered off. The filtrate was then concentrated and the residue was chromatographed on silica gel column eluted with heptanes to give the desired product, 3,5-dibromo-2-cyclohexyloxythiophene in good yield (25 g, 89% yield).

To a round bottom flask containing 3,5-dibromo-2-cyclohexyloxythiophene (25 g, 73.5 mmol) in tetrahydrofuran (480 nm) was added drop-wise n-BuLi (33 ml, 82.5 mmol, 2.5 molar in hexane) at −78° C., the resulting solution was stirred for one hour at such temperature, tributylborate (30 ml, 111 mmol) was slowly added to the mixture at −78° C., and the resulting mixture was stirred for an additional 1.5 hours. After warming the mixture to room temperature, aqueous sodium carbonate (20 weight %, 170 ml), iodobenzene (15 g, 73.5 mmol), and Pd(PPh$_3$)$_4$ (4.0 g) were added. The resulting mixture was heated under refluxed overnight. After cooling to room temperature, the mixture was extracted with ether, and the organic layers were combined and dried over sodium sulfate. The residue after solvent removal was purified (silica gel column, eluted with heptanes) to give the desired product (16.2 g, 65% yield).

To a round bottom flask containing 3-bromo-2-cyclohexloxy-5-phenylthiophene (15.7 g, 46.6 mmol) in tetrahydrofuran (125 ml) at −78° C. was added n-BuLi (20.5 ml, 50.5 mmol, 2.5 M in hexane) dropwise under nitrogen, and the solution was stirred at such temperature for 1.5 hours. Then, octafluorocyclopentene (3.1 ml, 22.2 mmol) was added slowly at −78° C., and the mixture was then stirred for 3 hours. The resulting mixture was then allowed to warm up to room temperature before water (20 ml) was added slowly to quench the reaction. The product was then extracted with ether and dried over magnesium sulfate, and the residue after solvent removal was chromatographed (silica gel) using heptanes as eluent to give the pure product as a light yellowish solid (7 g, 43.8% yield).

The colorless form of this dye in heptanes turned quickly to blue color when exposed with UV light (365 nm) and the blue color remained for days at room temperature under visible light.

Another useful synthesis is illustrated as follows for the preparation of 1,2-bis(2-ethoxy-5-phenyl-3-thienyl)perfluorocyclopentane.

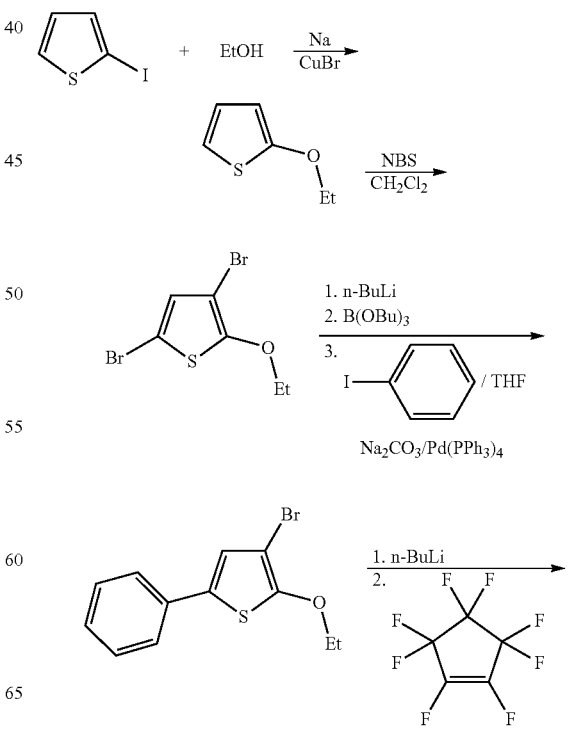

-continued

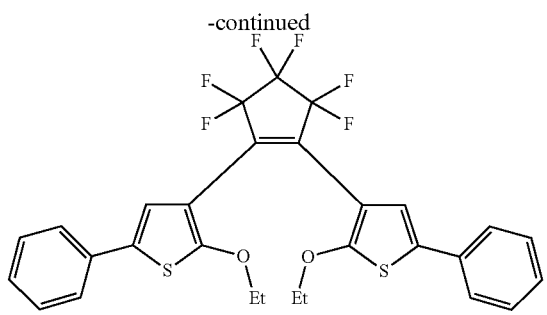

It is similar to the previous synthesis except that 2-ethoxythiophene is prepared in the first step in the following manner:

To a round bottom flask (1 liter) containing anhydrous ethanol (250 ml) was added sodium (22 g). After the sodium had completely disappeared, 2-bromothiophene (100 g) was added. The mixture was then heated to reflux under nitrogen, cuprous bromide (10 g) was added, and the resulting mixture was refluxed overnight. After cooling to room temperature, the mixture was filtered through a pad of silica gel eluted with hexane. The hexane solution was concentrated at room temperature under reduced pressure to give practically pure product (70 g, 89% yield).

INVENTION EXAMPLE 1

All amounts are parts by weight or weight %.

The colorless form of a photochromic compound prepared as described in the previous Synthesis was dissolved in diethylene glycol dimethyl ether to give a 1.8% solution. (Solution A). The following solution (Solution B) was prepared using the following components:

| | |
|---|---|
| Kodak Plate Finisher 850 | 30.0 |
| Water | 68 |
| Poly(acrylic acid, sodium salt) | 0.3 |
| Sodium ethyl hexyl sulfate | 0.4 |
| Citric acid | 0.17 |

Solution A (47 parts) was then added to 200 parts of Solution B. The final Solution C (developer) was then rubbed onto a negative-working lithographic printing plate precursor that had been imaged at 830 nm and 320 mJ/cm² using a commercially available Kodak® Trendsetter 3244x plate setter. This negative-working lithographic printing plate precursor was prepared using an electrochemically grained and phosphoric acid anodized aluminum substrate that had been treated with poly(acrylic acid), and that was coated with a photosensitive imageable layer formulation described in Example 18 of U.S. Pat. No. 7,261,998 (Hayashi et al.) that is incorporated herein by reference. A faint image appeared on the imaged precursor. The image, still wet with developer, was passed under a fluorescent light rich in UV (365 nm) and an immediate increase in color was observed. This color did not deteriorate over a period of more than two weeks.

COMPARATIVE EXAMPLE 1

Solution B from Invention Example 1 was used to develop a sample of the same negative-working lithographic printing plate precursor described in Invention Example 1 that had been imaged in the same manner. It was then exposed to UV light. The resulting image after this processing step was weak and did not improve when exposed to UV light.

The invention has been described in detail with particular reference to certain preferred embodiments thereof, but it will be understood that variations and modifications can be effected within the spirit and scope of the invention.

The invention claimed is:

1. A method of providing a lithographic printing member comprising:
   A) imagewise exposing a lithographic printing precursor comprising a substrate and an imageable layer to provide an imaged precursor having exposed and non-exposed regions in the imageable layer,
   B) contacting the imaged precursor with a coloration solution containing a photochromic compound, and
   C) exposing the imaged precursor after step B to ultraviolet (UV) light to effect color change of the photochromic compound attached to the imageable layer,
   wherein the photochromic compound is represented by the following Structure (I):

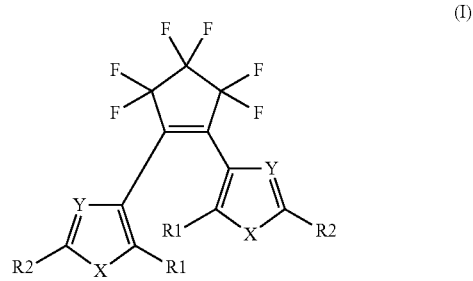

(I)

wherein X is oxygen, sulfur, sulfone, or a substituted or unsubstituted nitrogen, Y is oxygen or a substituted or unsubstituted carbon, $R^1$ is an electron donating group, and $R^2$ is hydrogen or any other substituent.

2. The method of claim 1 wherein the photochromic compound is stable at room temperature when exposed to 500 lumens of visible light for 100 hours.

3. The method of claim 1 wherein $R^1$ is an alkoxy group having at least 2 carbon atoms, cycloalkoxy group having at least 5 carbon atoms in the carbocyclic ring, aryloxy group having at least 6 carbon atoms in the carbocyclic ring, —S—$R^3$ wherein $R^3$ is a substituted or unsubstituted alkyl group having 1 to 6 carbon atoms, substituted or unsubstituted cycloalkyl group having 5 to 8 carbon atoms in the hydrocarbon ring, substituted or unsubstituted aryl group having 6 or 10 carbon atoms in the aromatic carbocyclic ring, or —Z'($R^4$)($R^5$) wherein Z' is a nitrogen atom, and $R^4$ and $R^5$ are the same or different substituted or unsubstituted alkyl groups having 1 to 5 carbon atoms, or substituted or unsubstituted aryl groups such as substituted or unsubstituted phenyl or naphthyl groups, and $R^2$ is hydrogen or an alkyl, aryl, cycloalkyl, alkoxy, cycloalkoxy, dialkylamino, or aryl group, or $R^2$ can be joined with the Y group on the same ring to form a fused ring system.

4. The method of claim 1 wherein $R^1$ an alkoxy group having at least 2 carbon atoms, cycloalkoxy group having at least 5 carbon atoms in the carbocyclic ring, or aryloxy group having at least 6 carbon atoms in the carbocyclic ring.

5. The method of claim 1 wherein the imaged precursor is processed in a developer prior to step B.

6. The method of claim 1 wherein the coloration solution used in step B is an acidic processing solution capable of developing the imaged precursor.

7. The method of claim 1 wherein the coloration solution used in step B is an alkaline processing solution capable of developing the imaged precursor.

8. The method of claim 1 wherein the imaged precursor is dried between steps B and C.

9. The method of claim 1 wherein the imaged precursor is dried after step C.

10. The method of claim 1 wherein the photochromic compound is added to the coloration solution just before its use in step B.

11. The method of claim 10 that is carried out in a processing machine wherein the photochromic compound is added to the coloration solution as the coloration solution is being circulated within the processing machine.

12. The method of claim 1 wherein the photochromic compound is present in the coloration solution in an amount of at least 0.005 weight % and up to and including 2 weight %.

13. The method of claim 1 wherein the coloration solution has a pH of from about 4 to about 7.5.

14. The method of claim 1 wherein the coloration solution comprises one or more organic solvents in an amount of from about 1 to about 25 weight %, the organic solvents being present to dissolve or disperse the photochromic compound.

15. The method of claim 1 wherein the UV exposure is carried out using UV radiation having a $\lambda_{max}$ of from about 350 nm to about 390 nm at 120 watts over an exposure width of 80 cm and a dwell time of from about 20 to about 90 seconds.

16. The method of claim 1 wherein the lithographic printing plate precursor is a negative-working lithographic printing plate precursor and the imageable layer is a negative-working imageable layer that comprises a free radically polymerizable component, a free radical initiator composition, a radiation absorbing compound, and a polymeric binder.

17. The method of claim 16 wherein the lithographic printing plate precursor is imagewise exposed either at a wavelength of from about 700 nm to about 1400 nm, or at a wavelength of from about 150 nm to about 450 nm.

18. The method of claim 16 wherein the lithographic printing plate precursor further comprises a water-soluble topcoat disposed on the negative-working imageable layer.

* * * * *